US012745892B2

(12) United States Patent
Suzuki et al.

(10) Patent No.: US 12,745,892 B2
(45) Date of Patent: Sep. 29, 2026

(54) WHITE BALANCE ADJUSTMENT JIG FOR ENDOSCOPE AND WHITE BALANCE ADJUSTMENT METHOD FOR ENDOSCOPE

(71) Applicant: FUJIFILM Corporation, Tokyo (JP)

(72) Inventors: Hiroaki Suzuki, Kanagawa (JP); Kenichi Otani, Kanagawa (JP); Yu Yoshimori, Kanagawa (JP); Shintaro Hattori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 18/474,256

(22) Filed: Sep. 26, 2023

(65) Prior Publication Data

US 2024/0108197 A1 Apr. 4, 2024

(30) Foreign Application Priority Data

Sep. 30, 2022 (JP) ................................ 2022-159000

(51) Int. Cl.
*A61B 1/06* (2006.01)
*A61B 1/00* (2006.01)
(Continued)

(52) U.S. Cl.
CPC .... *A61B 1/000095* (2022.02); *A61B 1/00057* (2013.01); *A61B 1/0655* (2022.02);
(Continued)

(58) Field of Classification Search
CPC ........ A61B 1/00; A61B 1/00121–0014; A61B 1/00057; A61B 2050/0079;
(Continued)

(56) References Cited

U.S. PATENT DOCUMENTS 5,820,547 A 10/1998 Strobl et al.
8,624,966 B2 * 1/2014 Ozawa ................ A61B 1/0638 348/68

(Continued)

FOREIGN PATENT DOCUMENTS

JP H0576483 3/1993
JP H05137693 6/1993

(Continued)

OTHER PUBLICATIONS

"Search Report of Europe Counterpart Application", issued on Feb. 15, 2024, p. 1-p. 8.

(Continued)

*Primary Examiner* — John W Miller
*Assistant Examiner* — Humam M Satti
(74) *Attorney, Agent, or Firm* — JCIPRNET

(57) ABSTRACT

A white balance adjustment jig for an endoscope includes: an insertion portion that includes at least one insertion hole into which a distal end part of an endoscope is inserted; a lid portion that is disposed to face the insertion portion; and an outer peripheral portion that is in contact with the insertion portion and the lid portion to form an internal space. The lid portion includes a chart having a plurality of marks on a surface on an insertion portion side, and the chart is inclined with respect to a perpendicular plane perpendicular to the insertion direction of the distal end part.

22 Claims, 23 Drawing Sheets

(51) Int. Cl.
*H04N 23/50* (2023.01)
*H04N 23/56* (2023.01)
*H04N 23/88* (2023.01)

(52) U.S. Cl.
CPC ........... *H04N 23/555* (2023.01); *H04N 23/56* (2023.01); *H04N 23/88* (2023.01)

(58) Field of Classification Search
CPC ............ A61B 1/000095; A61B 1/0655; H04N 23/555; H04N 23/56; H04N 23/88
See application file for complete search history.

(56) References Cited

U.S. PATENT DOCUMENTS

| | | | | |
|---|---|---|---|---|
| 2010/0245541 | A1 * | 9/2010 | Zhao | H04N 13/246 348/E13.001 |
| 2013/0085329 | A1 * | 4/2013 | Morrissette | A61B 1/00057 600/111 |
| 2014/0267656 | A1 | 9/2014 | Blanquart | |
| 2019/0028614 | A1 | 1/2019 | De Paepe et al. | |
| 2019/0374155 | A1 * | 12/2019 | Wang | A61B 1/2736 |

FOREIGN PATENT DOCUMENTS

| | | | | |
|---|---|---|---|---|
| JP | 2006223591 | A * | 8/2006 | A61B 1/00057 |
| JP | 2010200880 | | 9/2010 | |
| JP | 2020032201 | | 3/2020 | |

OTHER PUBLICATIONS

"Office Action of Europe Counterpart Application", issued on Feb. 25, 2025, p. 1-p. 5.
"Notice of Reasons for Refusal of Japan Counterpart Application", issued on Mar. 3, 2026, with English translation thereof, p. 1-p. 17.
"Notice of Reasons for Refusal of Japan Counterpart Application", issued on Jun. 9, 2026, with English translation thereof, p. 1-p. 10.

* cited by examiner

WHITE BALANCE ADJUSTMENT JIG FOR ENDOSCOPE AND WHITE BALANCE ADJUSTMENT METHOD FOR ENDOSCOPE

CROSS-REFERENCE TO RELATED APPLICATIONS

This application claims priority under 35 U.S.C § 119(a) to Japanese Patent Application No. 2022-159000 filed on 30 Sep. 2022. The above application is hereby expressly incorporated by reference, in its entirety, into the present application.

BACKGROUND OF THE INVENTION

1. Field of the Invention

The present invention relates to a white balance adjustment jig for an endoscope and a white balance adjustment method for an endoscope.

2. Description of the Related Art

In the medical field, observation of an inside of a body, endoscopic surgery, and the like are performed using an endoscope. In the endoscope, various electronic components for generating an image through imaging, and the like, including an imaging element for imaging an observation target, are used. Some of these components and the like have individual differences, degradation over time, and the like, which may result in not obtaining an appropriate image as they are. In addition, individual differences, degradation over time, and the like may also occur in a light source used for imaging the observation target. In order to eliminate these problems and obtain an appropriate image, calibration such as white balance is performed for the endoscope.

The white balance may be adjusted by imaging white sterilized gauze, for example, in a rigid endoscope used for endoscopic surgery, and the like. In addition, a method is known in which a white cap is provided on a distal end part of an endoscope (JP2020-032201A (corresponding to US2014/267656A1) and JP2010-200880A). Further, it is known that white balance is adjusted by using a white balance adjustment tool having a cap-like shape (JP1993-076483A (JP-H05-076483A)).

SUMMARY OF THE INVENTION

There are various types of endoscopes used in the medical field depending on the use, purpose, and the like. Therefore, for example, in a case where, in an image captured by an endoscope (hereinafter referred to as an endoscope image), a more precisely adjusted color temperature is required for the endoscope image, white balance adjustment using white sterilized gauze may not be sufficient. In addition, there are various types of endoscopes in terms of the form of the endoscope, and the endoscopes are broadly classified into a rigid endoscope and a flexible endoscope. Further, various types of endoscopes are also used in each of the rigid endoscope and the flexible endoscope. However, in some cases, the white balance adjustment tool conventionally used cannot be universally used appropriately for various types of endoscopes.

An object of the present invention is to provide a white balance adjustment jig for an endoscope and a white balance adjustment method for an endoscope that enable appropriate white balance adjustment for any of a plurality of types of endoscopes.

According to the present invention, there is provided a white balance adjustment jig for an endoscope, comprising: an insertion portion that includes at least one insertion hole into which a distal end part of an endoscope is inserted; a lid portion that is disposed to face the insertion portion in an insertion direction of the distal end part; and an outer peripheral portion that is in contact with the insertion portion and the lid portion to form an internal space with the insertion portion and the lid portion, in which the lid portion includes a chart having a plurality of marks on an inner surface facing the internal space, and the chart is inclined with respect to a perpendicular plane perpendicular to the insertion direction.

It is preferable that the chart is inclined at an angle within a range of 5 degrees or more and 40 degrees or less with respect to the perpendicular plane.

It is preferable that the chart is inclined at an angle within a range of 15 degrees or more and 30 degrees or less with respect to the perpendicular plane.

It is preferable that the chart is inclined toward an insertion portion side.

It is preferable that the angle is an angle in a case where an inclination toward an insertion portion side is defined as positive with a lower part of the chart in use as an axis.

It is preferable that the chart is inclined at an angle within a range of 5 degrees or more and 40 degrees or less with respect to a perpendicular plane perpendicular to an optical axis of the endoscope in a case where an inclination toward an insertion portion side is defined as positive with a lower part of the chart in use as an axis.

It is preferable that the chart is inclined at an angle within a range of 15 degrees or more and 30 degrees or less with respect to the perpendicular plane in a case where an inclination toward an insertion portion side is defined as positive with a lower part of the chart in use as an axis.

It is preferable that the plurality of marks are disposed in the chart along the insertion direction.

It is preferable that the insertion portion includes a plurality of the insertion holes, and that one of the plurality of marks is disposed at a position where the chart and an optical axis direction of the endoscope to be inserted into the insertion hole intersect with each other.

It is preferable that the insertion portion includes a plurality of the insertion holes, and that the plurality of insertion holes have inner diameters different from each other.

It is preferable that the insertion portion includes a plurality of the insertion holes, and that the internal space is partitioned according to each of the insertion holes.

It is preferable that the lid portion and the outer peripheral portion are separably connected to each other.

It is preferable that the lid portion and the outer peripheral portion are separably connected to each other by magnetic force and/or fitting.

It is preferable that the lid portion includes the chart and a light shielding member, and that, in a case where the lid portion is disposed to face the insertion portion, the chart and the light shielding member are provided in this order from an insertion portion side.

It is preferable that the lid portion is configured such that the chart and the light shielding member are separable from each other.

It is preferable that the lid portion includes a lid portion base and the chart, and that the light shielding member is the lid portion base.

It is preferable that the endoscope is a rigid endoscope.

It is preferable that the endoscope is a direct-viewing endoscope or an oblique-viewing endoscope.

It is preferable that the mark has a reference color.

In addition, according to the present invention, there is provided a white balance adjustment method for an endoscope using a white balance adjustment jig for an endoscope, the white balance adjustment jig including an insertion portion that includes at least one insertion hole into which a distal end part of an endoscope is inserted, a lid portion that is disposed to face the insertion portion in an insertion direction of the distal end part, and an outer peripheral portion that is in contact with the insertion portion and the lid portion to form an internal space with the insertion portion and the lid portion, the lid portion including a chart having a plurality of marks on an inner surface facing the internal space, the chart being inclined with respect to a perpendicular plane perpendicular to the insertion direction, the white balance adjustment method comprising: inserting the distal end part of the endoscope including an imaging unit that images a subject into the insertion hole; imaging the mark using the imaging unit; and adjusting white balance of the endoscope using an image showing the mark, which is obtained through imaging.

It is preferable that the endoscope is a direct-viewing endoscope or an oblique-viewing endoscope.

It is preferable that the white balance adjustment jig for an endoscope includes a plurality of the insertion holes, and that the distal end part is inserted into the insertion hole selected from the plurality of insertion holes according to an outer diameter of the distal end part.

It is preferable that the mark is imaged after adjusting a position and a shape of the mark shown in the image.

According to the present invention, it is possible to perform appropriate white balance adjustment for any of a plurality of types of endoscopes.

Figure 23:
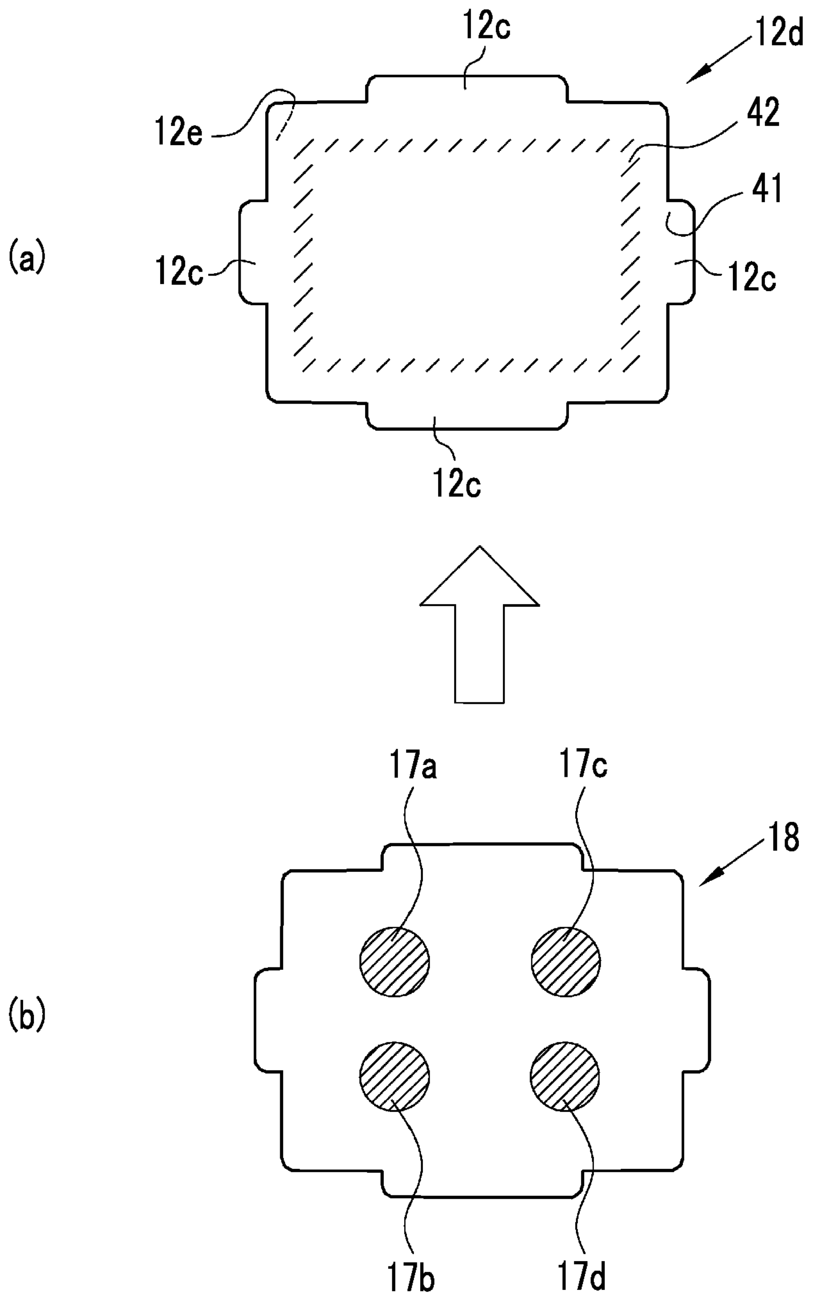

(a) of FIG. 23 is an explanatory diagram illustrating a light shielding member separated from the chart, and (b) of FIG. 23 is an explanatory diagram illustrating the chart separated from the light shielding member.

Figure 24:
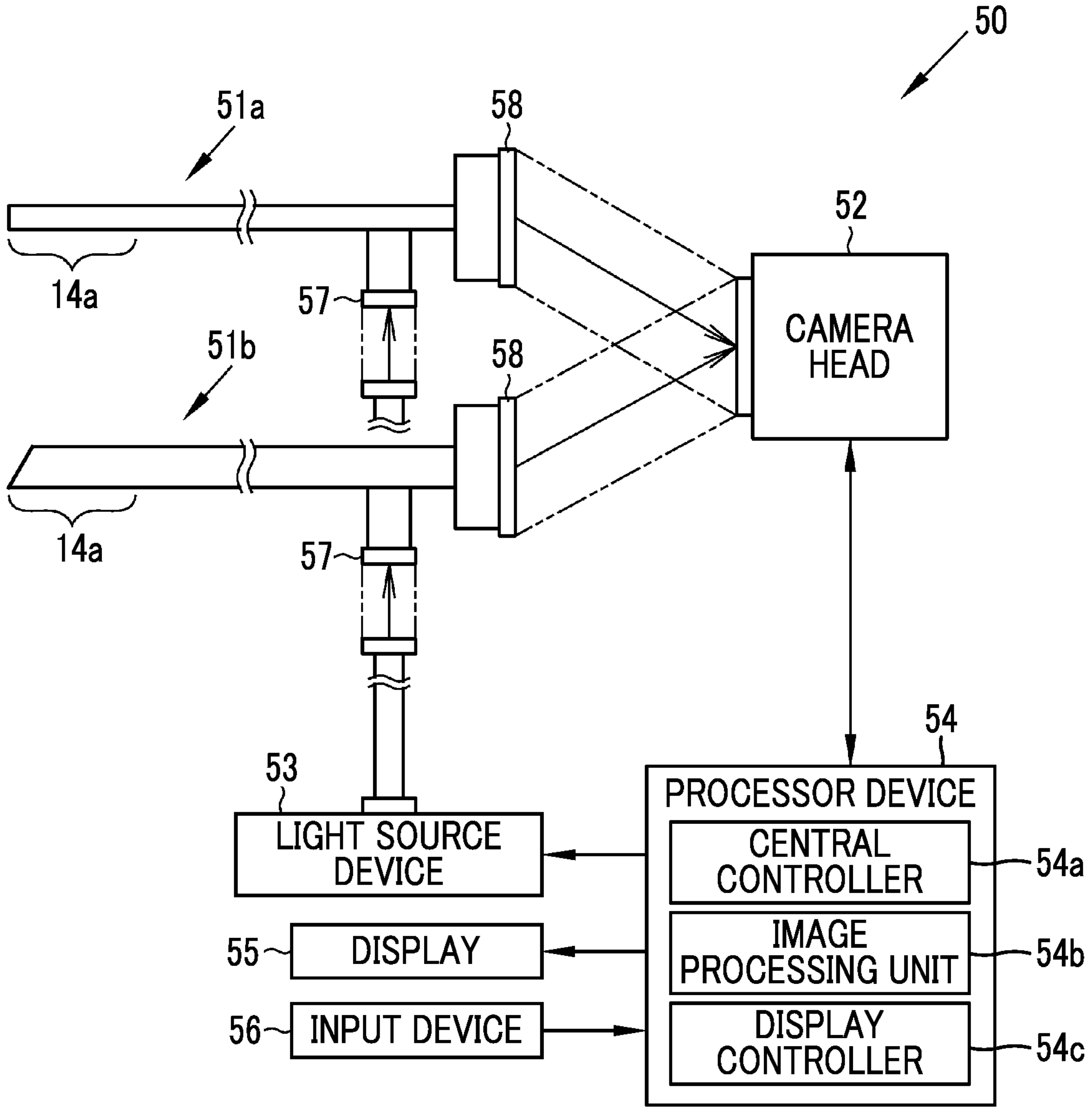

FIG. 24 is an explanatory diagram illustrating a configuration of an endoscope system.

Figure 25:
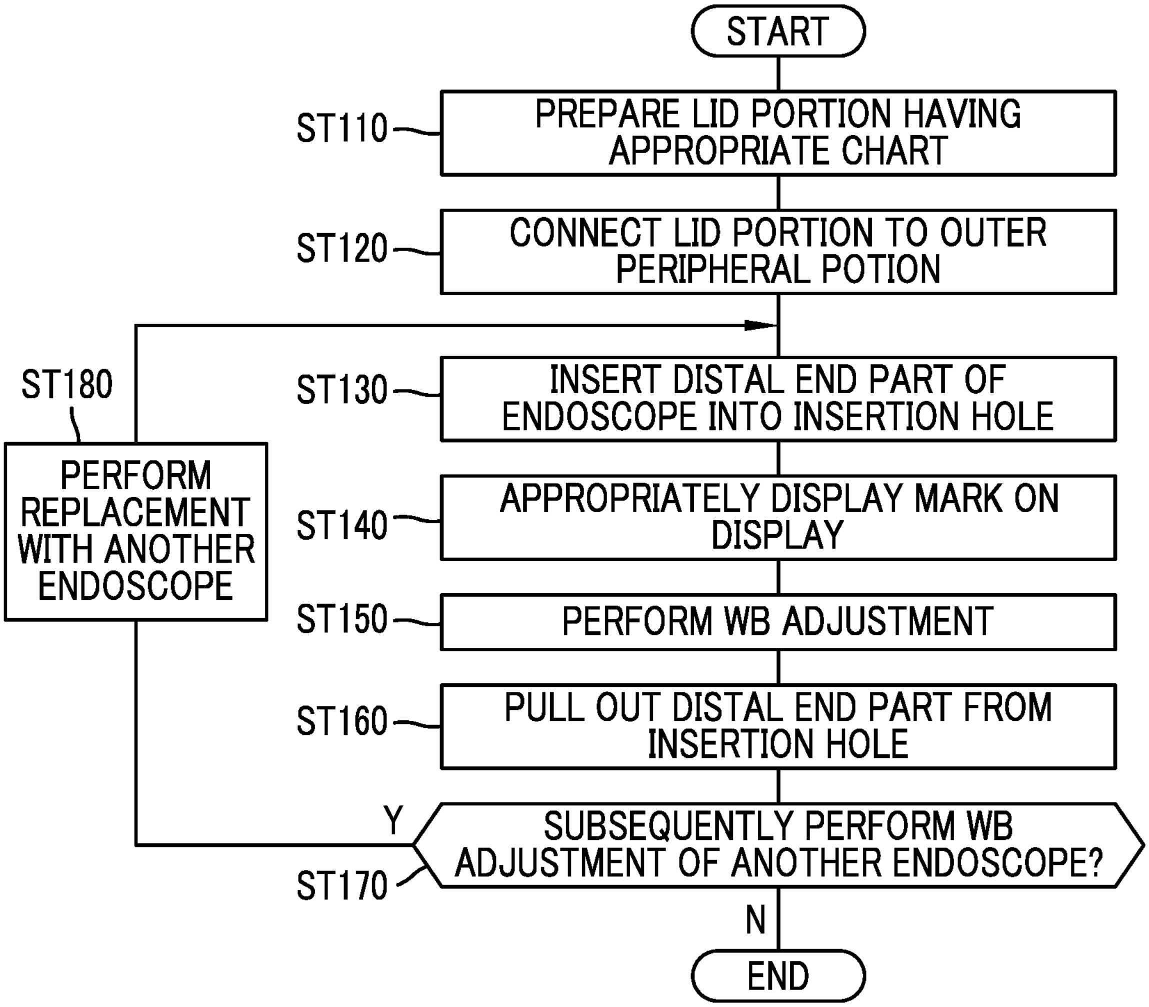

FIG. 25 is a flowchart illustrating a flow of performing white balance adjustment of the endoscope using the white balance adjustment jig for an endoscope.

Figure 26A:
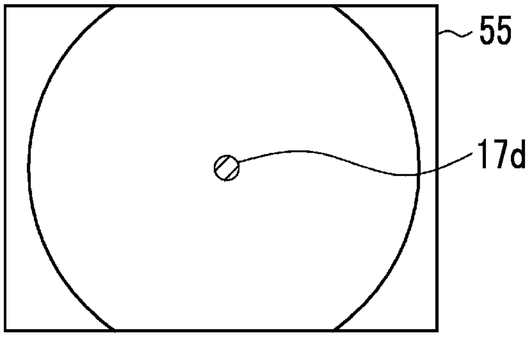
Figure 26B:
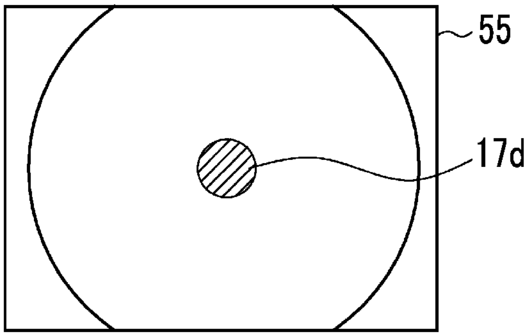
Figure 26C:
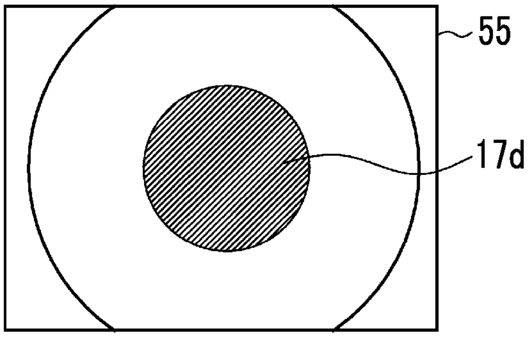

FIGS. 26A to 26C are each an image diagram of the mark displayed on a display according to a difference in a position of the distal end part in an internal space, in which FIG. 26A shows a case where the distal end part and the chart are far apart from each other, FIG. 26B shows a case where the distal end part and the chart are slightly far apart from each other, and FIG. 26C shows a case where a distance between the distal end part and the chart is appropriate.

Figure 27:
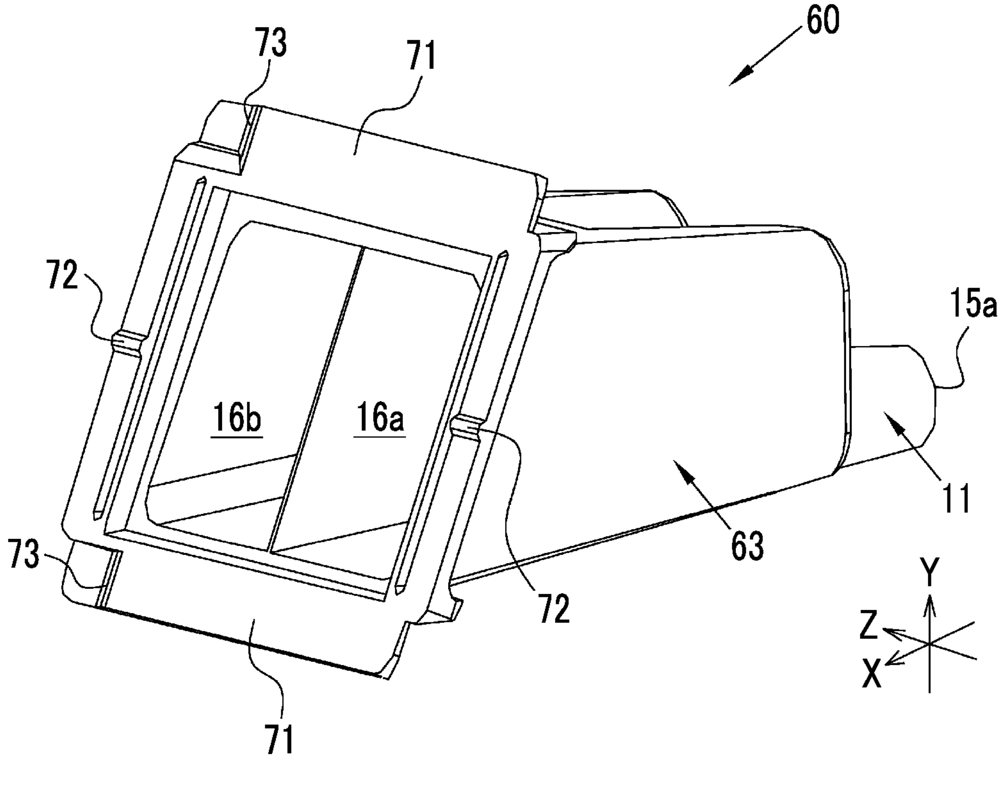

FIG. 27 is a perspective view of a white balance adjustment jig for an endoscope of a second embodiment in which a lid portion is separated.

Figures 28A, 28B, 28C:
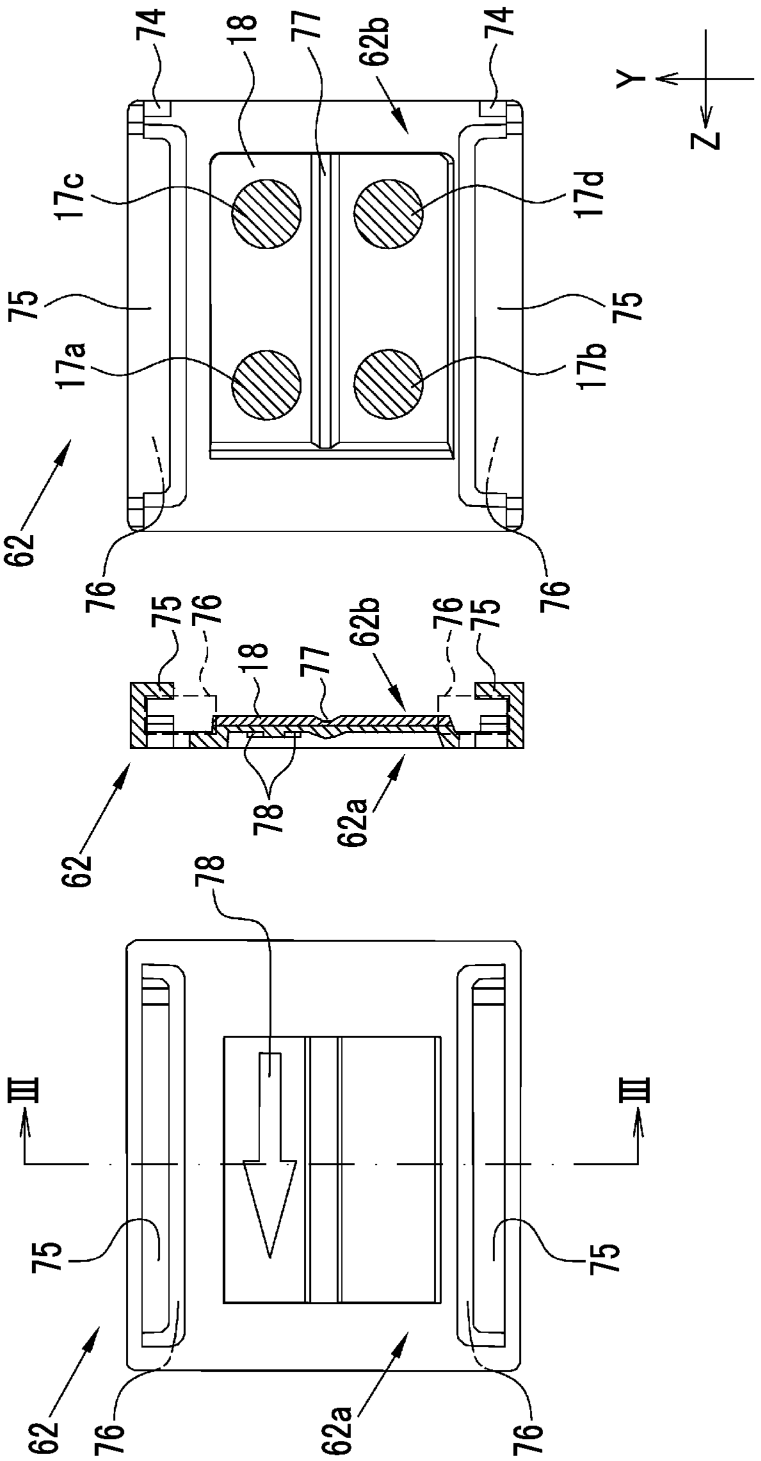

FIGS. 28A to 28C show the lid portion of the white balance adjustment jig for an endoscope of the second embodiment, in which FIG. 28A is a front view of the lid portion illustrating an outer surface of the lid portion, FIG. 28B is a cross-sectional view cut along line of III-III of FIG. 28A, and FIG. 28C is a rear view of the lid portion illustrating an inner surface of the lid portion.

Figure 29:
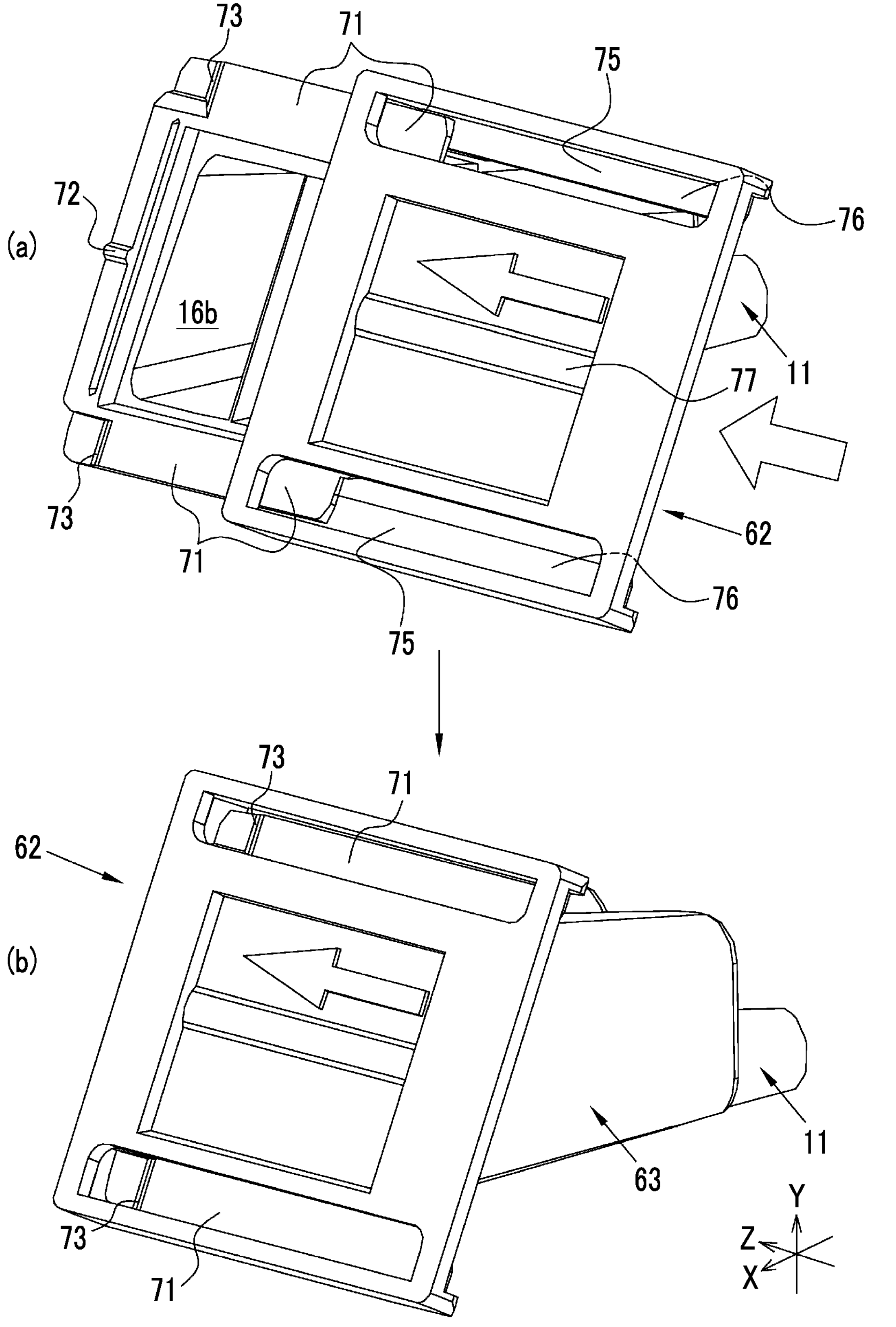

FIG. 29 is an explanatory diagram illustrating connection between the lid portion and an outer peripheral portion of the second embodiment, in which (a) of FIG. 29 represents an intermediate stage of the connection between the lid portion and the outer peripheral portion and (b) of FIG. 29 represents completion of the connection between the lid portion and the outer peripheral portion.

Figure 30:
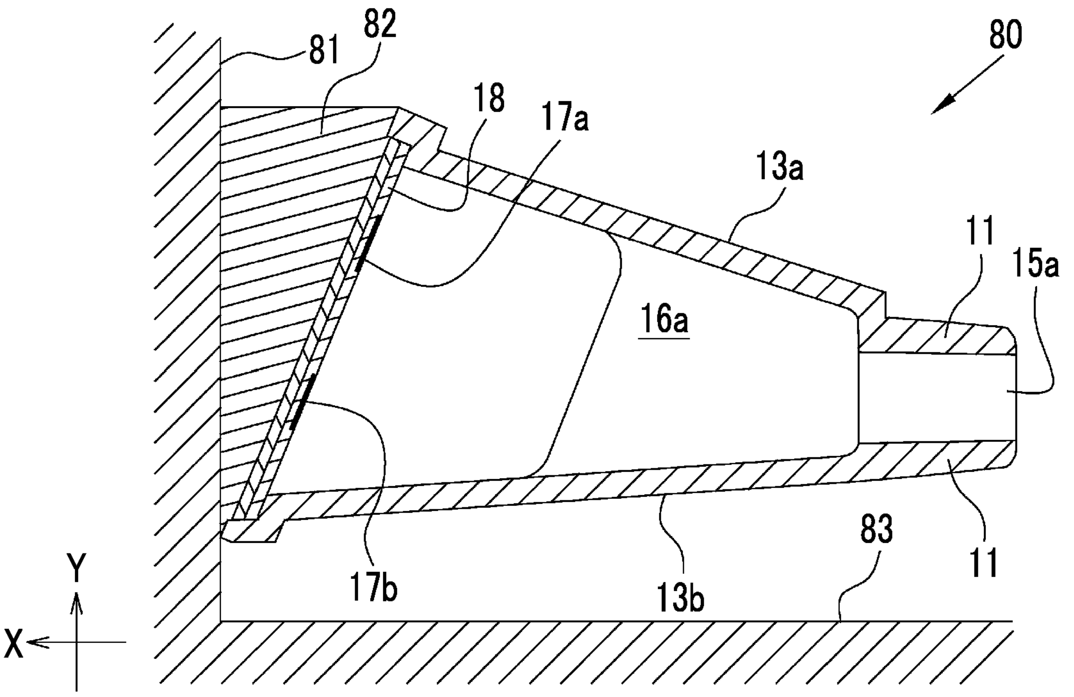

FIG. 30 is an explanatory diagram illustrating an example of an installation example in a case where the white balance adjustment jig for an endoscope is installed.

Figure 31:
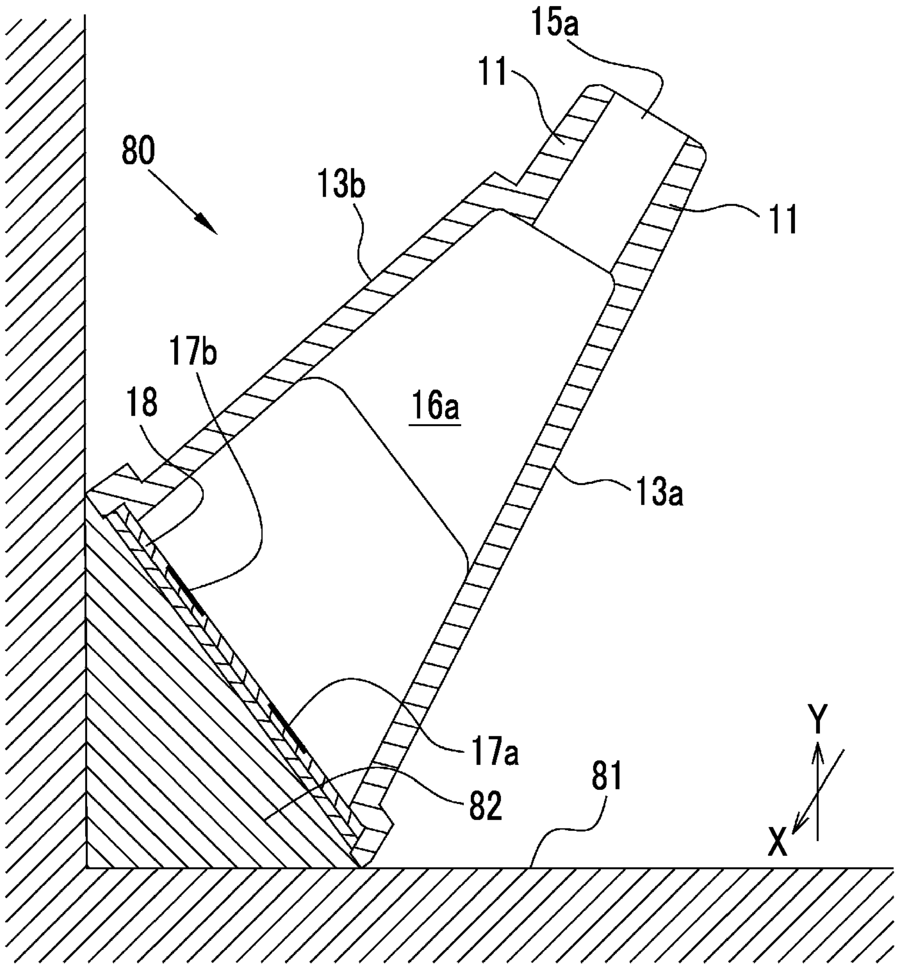

FIG. 31 is an explanatory diagram illustrating another example of the installation example in a case where the white balance adjustment jig for an endoscope is installed.

Figure 32A:
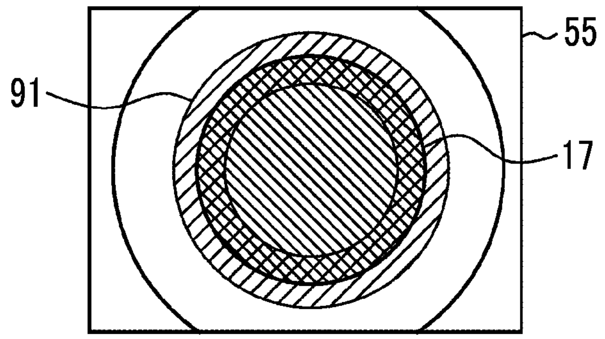
Figure 32B:
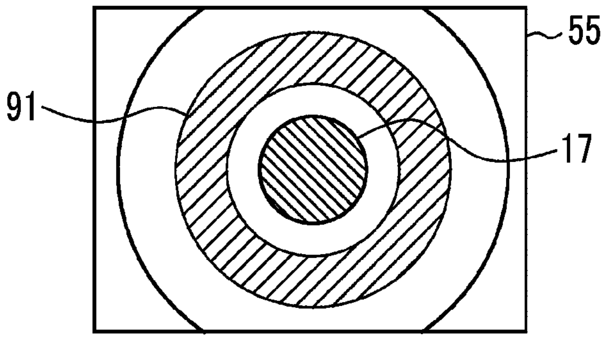
Figure 32C:
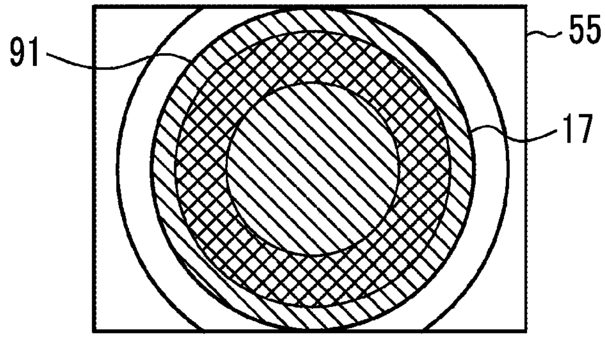
Figure 32D:
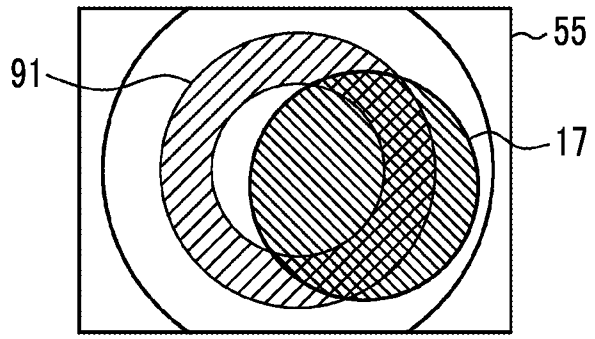

FIGS. 32A to 32D are image diagrams illustrating a case where a determination display is displayed on the display, in which FIG. 32A shows a case where the disposition of the distal end part is appropriate, FIG. 32B shows a case where the distal end part and the chart are far apart from each other, FIG. 32C shows a case where the distal end part and the chart are close to each other, and FIG. 32D shows a case where the distance between the distal end part and the chart is appropriate but the direction of the distal end part deviates.

DESCRIPTION OF THE PREFERRED EMBODIMENTS

Hereinafter, embodiments will be described with reference to the drawings as appropriate. First, the background leading to obtaining one aspect of the following embodiment will be described. In recent years, image processing has been performed on an endoscope image to acquire various pieces of information that can be useful for diagnosis or the like, such as biological information of a subject, extraction of a lesion part, and differential information of the extracted lesion part. For example, as disclosed in JP2015-091467A and the like, there is known a technique of using an endoscope image to extract a low oxygen part having a low oxygen saturation in a subject and of displaying the low oxygen part on the endoscope image.

In the endoscope image used for image extraction of the low oxygen part in the subject, it is necessary to severely perform white balance adjustment for color, that is, to precisely adjust color rendering at a color temperature. This is because the numerical value of the oxygen saturation varies depending on a color difference of the endoscope image. Therefore, it has been considered preferable to use a dedicated chart for each of various endoscopes in order to perform precise white balance adjustment.

Therefore, in a case where white balance adjustment is performed using a dedicated chart for each of a plurality of types of endoscopes, respective charts are required according to the types of endoscopes, which may lead to complicated operation such as handling dedicated charts corresponding to the various endoscopes. In addition, it is also considered that using a plurality of charts may cause an occurrence of errors such as using a chart that does not correspond to a specific endoscope, which may lead to white balance adjustment performed based on erroneous contents.

Further, in order to precisely perform the white balance adjustment, it is important to appropriately adjust imaging conditions, such as a distance between a chart and a distal end surface of an endoscope provided in an objective lens of the endoscope, and an angle, in the imaging during the white balance adjustment. As described above, in various endoscopes, preparing charts according to respective types of endoscopes during the white balance adjustment and imaging the chart after adjusting the imaging condition to an appropriate imaging condition may be time-consuming and lead to complicated adjustment.

Among the respective types of endoscopes, particularly in a rigid endoscope of a camera head system, a combination of the rigid endoscope, which is a scope, a camera head, and a light source is decided on immediately before use, and white balance cannot be pre-adjusted (pre-calibrated) during shipment or installation, unlike a flexible endoscope. Therefore, prior to each procedure, a doctor or the like who is a user needs to adjust the white balance for each of a plurality of rigid endoscopes to be used. Accordingly, in the white balance adjustment in the rigid endoscope, particularly in the white balance adjustment of the rigid endoscope capable of the image extraction of the low oxygen part, as described above, it is necessary to prepare charts corresponding to various endoscopes and to individually image the chart based on an appropriate imaging condition for each endoscope, which is time-consuming.

Hereinafter, embodiments related to a white balance adjustment jig for an endoscope and a white balance adjustment method for an endoscope that enable appropriate white balance adjustment for any of a plurality of types of endoscopes will be described.

First Embodiment

Figure 1:
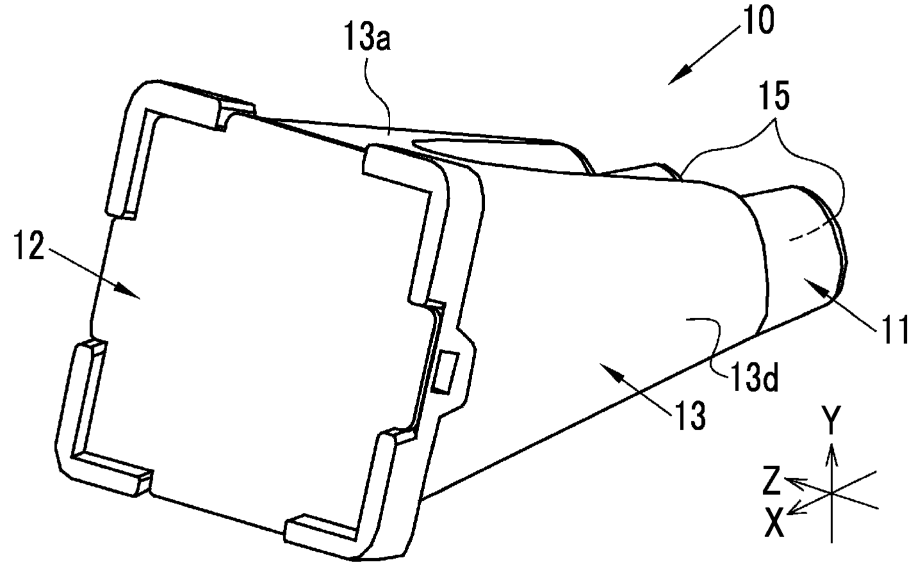
FIG. 1 is a perspective view of a white balance adjustment jig for an endoscope in which a lid portion is displayed.

As shown in FIG. 1, a white balance adjustment jig for an endoscope (hereinafter referred to as an adjustment jig) 10 is a tool used for white balance adjustment of a plurality of types of endoscopes and comprises an insertion portion 11, a lid portion 12, and an outer peripheral portion 13. The outer peripheral portion 13 includes a left side surface part 13*d*, an upper surface part 13*a*, a bottom surface part 13*b* (see FIG. 5), and a right side surface part 13*c* (see FIG. 6). The adjustment jig 10 has a box-like shape composed of the insertion portion 11, the lid portion 12, and the outer peripheral portion 13 and has an internal space 16 (see FIG. 5) inside. The internal space 16 may consist of internal spaces 16*a* and 16*b* (see FIG. 6), and the internal spaces 16*a* and 16*b* are referred to as the internal space 16 in a case where these are not distinguished.

Figure 2:
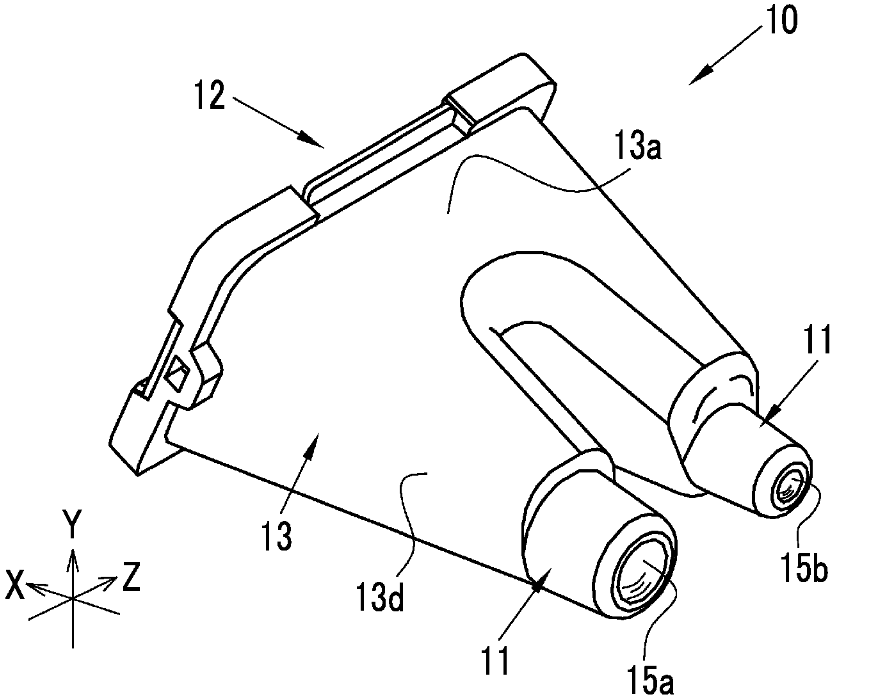
FIG. 2 is a perspective view of the white balance adjustment jig for an endoscope in which insertion holes are displayed.

As shown in FIG. 2, the insertion portion 11 is provided with at least one insertion hole 15 into which a distal end part (see FIG. 3, hereinafter referred to as a distal end part) 14*a* of an endoscope 14 is inserted. The insertion hole 15 may consist of insertion holes 15*a* and 15*b*, and the insertion holes 15*a* and 15*b* are referred to as the insertion hole 15 in a case where these are not distinguished. The distal end part 14*a*, which is inserted into the insertion hole 15 in an insertion direction X, is further inserted to an appropriate position of the internal space 16 and images a chart 18 (see FIG. 5) provided on the lid portion 12 on an internal space 16 side. The white balance adjustment of the endoscope is performed using an endoscope image obtained by imaging the chart 18.

The insertion portion 11 may be provided with a plurality of the insertion holes 15. It is preferable that the plurality of insertion holes 15 have inner diameters that are different from each other according to outer diameters of the distal end parts 14*a*, which are different depending on the type of endoscopes 14 to be inserted. As a result, in a case where the white balance adjustment is performed for each of a plurality of types of endoscopes 14, it is possible to prevent light from entering the internal space 16 through the insertion hole 15, a guide function of allowing the distal end part 14*a* to advance to an appropriate position is exhibited, it is possible to appropriately image the chart 18, and it is possible to appropriately adjust the white balance. The plurality of types of endoscopes 14 used herein are the types that are distinguished by the outer diameter of the distal end part 14*a*. Specific examples thereof include a large diameter endoscope 14*c* in which the outer diameter of the distal end part 14*a* is relatively large, and a small diameter endoscope 14*d* in which the outer diameter of the distal end part 14*a* is relatively small (see FIGS. 9A and 9B).

In addition, in order to ensure ease of insertion, a movable range for positioning adjustment of a distal end surface 14*b* (see FIG. 3) when imaging the chart 18, and the like, it is preferable for the inner diameter of the insertion hole 15 to be as small as possible while allowing for a moderate gap between the distal end part 14*a* and the insertion hole 15 in a case where the distal end part 14*a* is inserted into the insertion hole 15. As a result, it is possible to achieve both ensuring a function of the insertion portion 11 to guide the insertion of the distal end part 14*a* for positioning adjustment of the distal end surface 14*b* and restraining light from entering the internal space 16 through the gap between the distal end part 14*a* and the insertion hole 15.

The insertion portion 11 is provided with two insertion holes 15, that is, a first insertion hole 15*a* and a second insertion hole 15*b*, having inner diameters different from each other, and the first insertion hole 15*a* has an inner diameter larger than that of the second insertion hole 15*b*. For example, the inner diameter of the first insertion hole 15*a* is 11 mm at the inlet, and the inner diameter of the second insertion hole 15*b* is 6 mm at the inlet.

Figure 3:
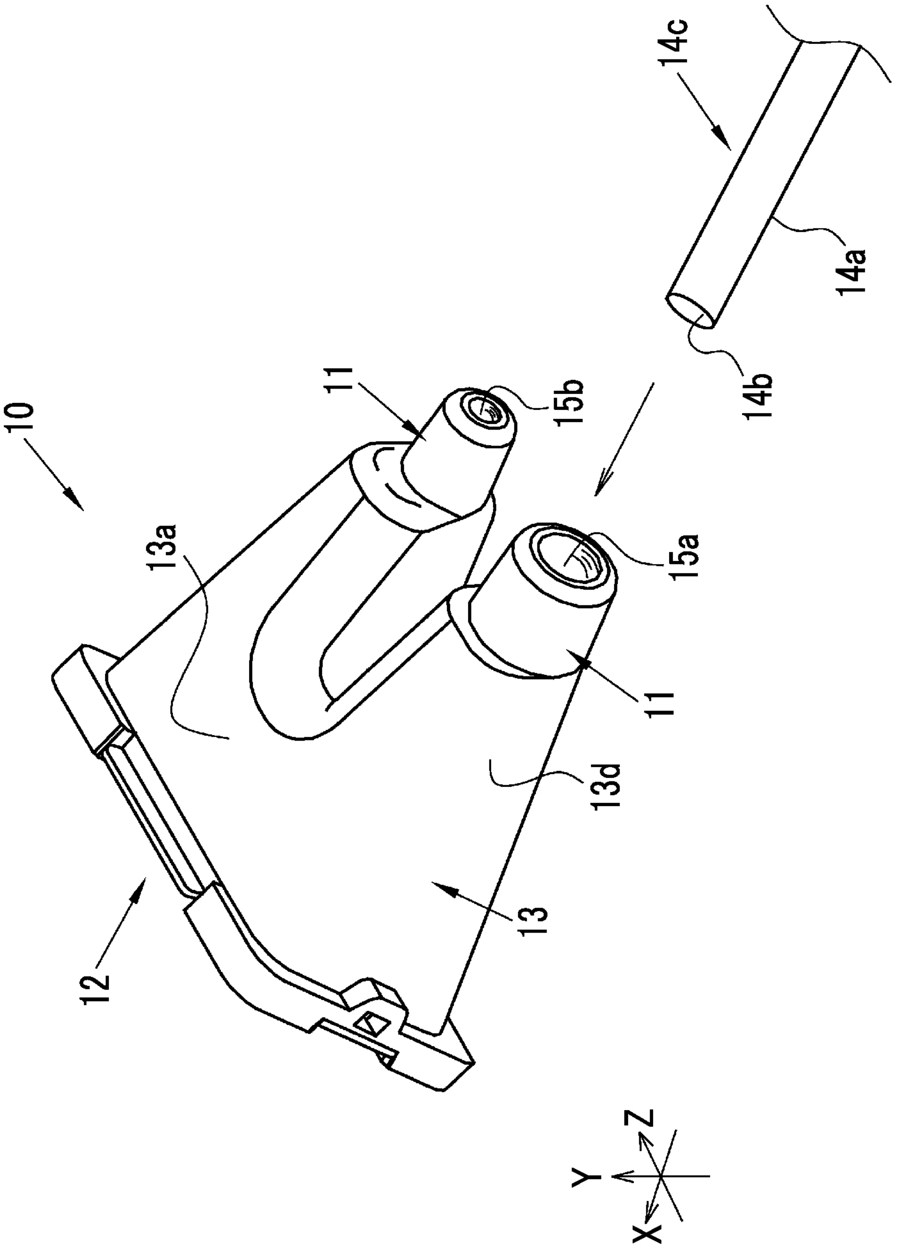
FIG. 3 is an explanatory diagram of a case where a distal end part of an endoscope is inserted into an insertion hole having a larger inner diameter.
Figure 4:
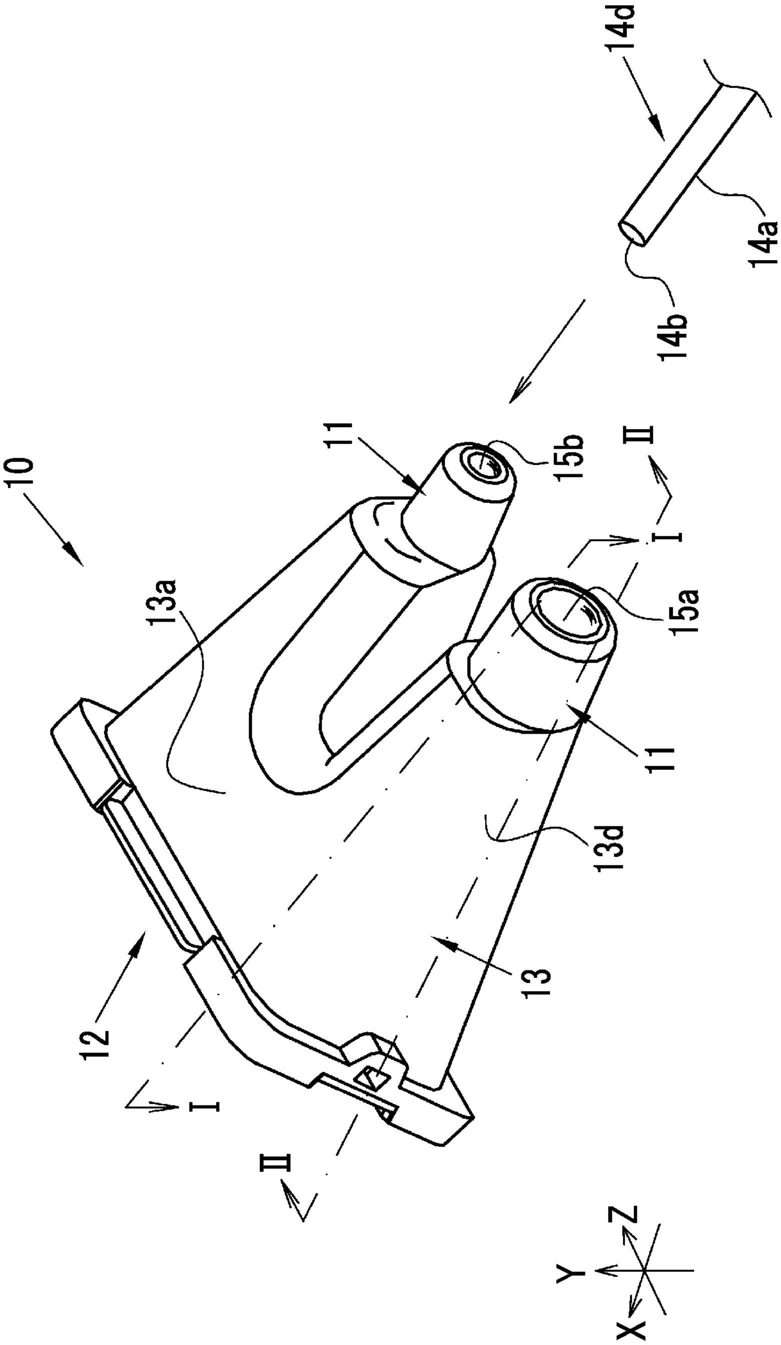
FIG. 4 is an explanatory diagram of a case where the distal end part of the endoscope is inserted into an insertion hole having a smaller inner diameter.

The distal end part 14*a* is inserted into the insertion hole 15 selected according to the outer diameter of the distal end part 14*a* to be inserted. As shown in FIG. 3, in a case where the endoscope is the large diameter endoscope 14*c* in which an outer diameter d1 (see FIG. 9A) of the distal end part 14*a* is within a range of more than 5 mm and 10 mm or less, the distal end part 14*a* is inserted into the first insertion hole 15*a*. Further, as shown in FIG. 4, in a case where the endoscope is the small diameter endoscope 14*d* in which an outer diameter d2 (see FIG. 9B) of the distal end part 14*a* is 5 mm or less, the distal end part 14*a* is inserted into the second insertion hole 15*b*.

Figure 5:
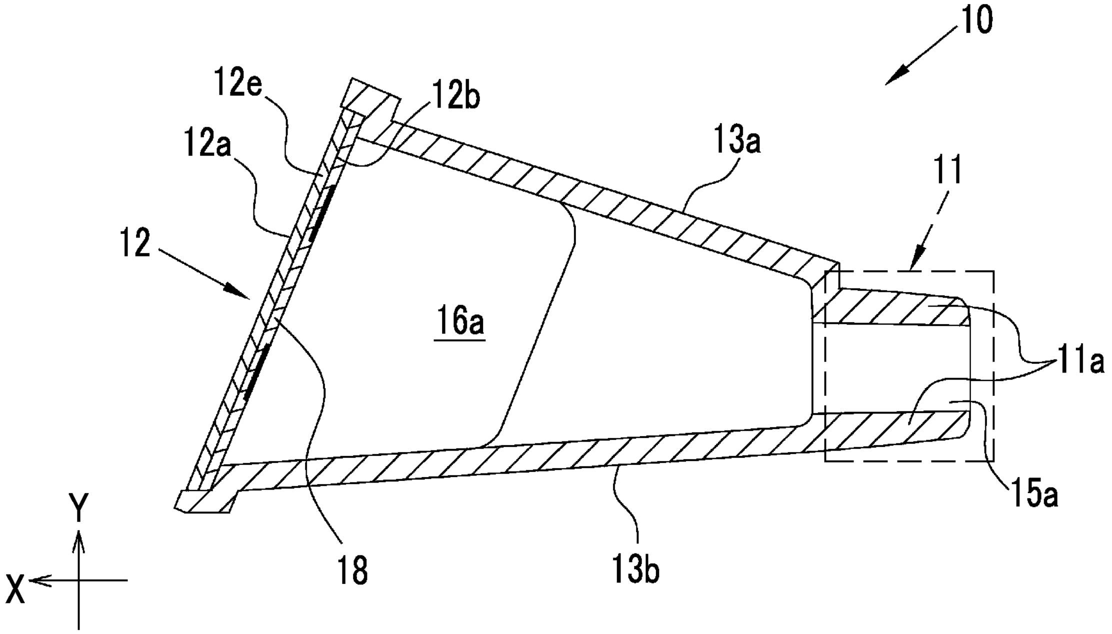
FIG. 5 is a cross-sectional view cut along line I-I of FIG. 4.

As shown in FIG. 5, the insertion portion 11 may be configured by a guide part 11*a*. The guide part 11*a* has a guide function in a case where the user inserts the distal end part 14*a* into the insertion hole 15. The guide part 11*a* can have a tubular shape in which a longitudinal direction is the insertion direction X. By forming the tubular guide part 11*a*, a part of a bottom, an outer surface, or the like of the distal end part 14*a* is inserted while naturally coming into contact with a part of a bottom, an inner surface, or the like of the tubular insertion hole 15 in a case where the user inserts the distal end part 14*a*, which facilitates more appropriate insertion of the distal end part 14*a* toward the lid portion 12. In addition, it becomes possible for the user to more easily dispose the distal end surface 14*b* of the endoscope 14 at an appropriate position in the internal space 16.

Figure 6:
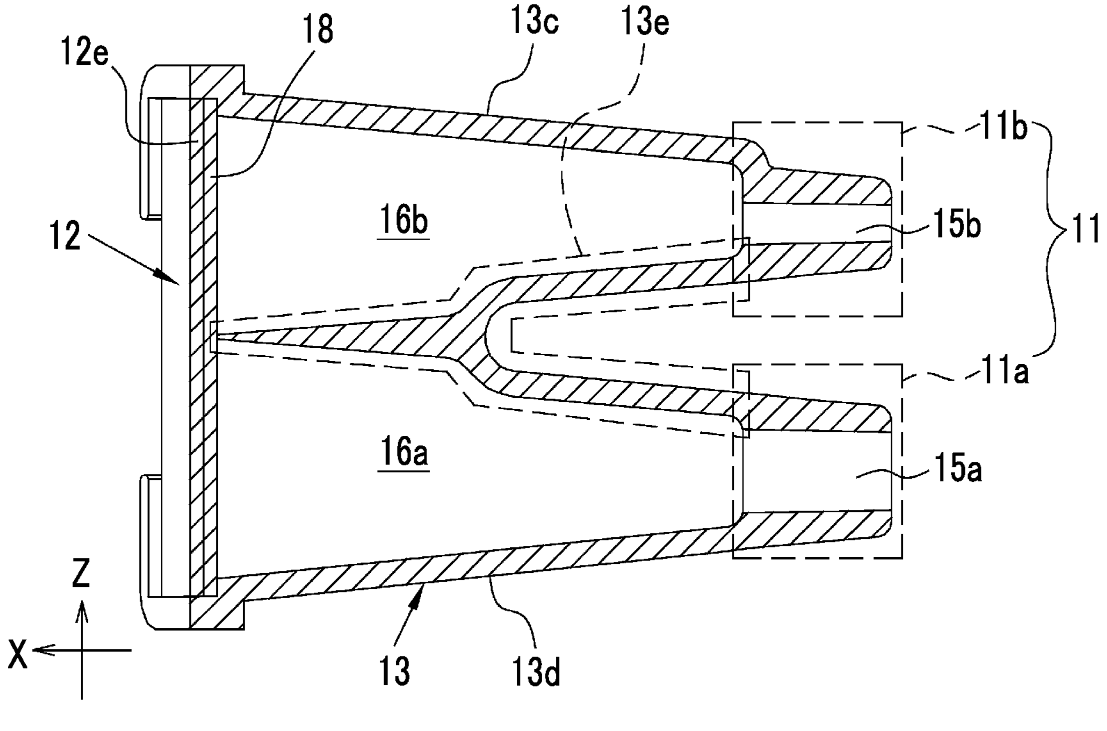
FIG. 6 is a cross-sectional view cut along line II-II of FIG. 4.

As shown in FIG. 6, the guide part 11*a* and a guide part 11*b* each may have a tapered shape in which the inner diameter thereof slightly increases from the inlet of the insertion hole 15 toward the lid portion 12 along the insertion direction X. The inner diameter of the inlet of the first insertion hole 15*a* is 11 mm, but the outlet of the first insertion hole 15*a*, which is located closest to the lid portion 12 in the guide part 11*a* along the insertion direction X, is 12 mm. Similarly, the inner diameter of the inlet of the second insertion hole 15*b* is 6 mm, but the outlet of the second insertion hole 15*b*, which is located closest to the lid portion 12 in the guide part 11*b* along the insertion direction X, is 7 mm. By providing the guide part 11*a* and the guide part 11*b* that are tapered along the insertion direction X, it becomes possible to easily dispose the distal end part 14*a* by performing positioning adjustment at a position where a mark 17 (see FIG. 8B) can be appropriately imaged in a case where the user inserts the distal end part 14*a* into the insertion hole 15, and it is possible to ensure the movable range for positioning adjustment of the distal end surface 14*b* of the endoscope 14 in a case where the distal end part 14*a* images the chart 18.

In addition, in a case where the insertion portion 11 is provided with the plurality of insertion holes 15, the internal space 16 may be partitioned according to each of the insertion holes 15. In a case where the plurality of insertion holes 15 are provided, a partition 13*e* partitions the internal space 16 into an internal space 16*a* connected to the first insertion hole 15*a* and an internal space 16*b* connected to the second insertion hole 15*b*. As a result, it is possible to prevent light from entering the internal space 16 through the insertion hole 15 into which the distal end part 14*a* is not inserted. Accordingly, the internal space 16 in which the entry of external light is restrained allows for the imaging of the chart 18 under an appropriate imaging condition for white balance adjustment.

In addition, it is preferable that the partition 13*e* has a shape such that it can better block the entry of light through the insertion hole 15 into which the distal end part 14*a* is inserted. Therefore, it is preferable that the partition 13*e* is in contact with the inner surface of the lid portion 12 facing the internal space. In addition, the partition 13*e* may be configured by extending the guide part 11*a* in a tubular shape corresponding to each insertion hole 15.

The lid portion 12 is disposed to face the insertion portion 11 in the insertion direction X of the distal end part 14*a* in the insertion hole 15. The lid portion 12 functions as a constituent portion that constitutes a part of a housing of the adjustment jig 10 and as a chart holding portion that holds the chart 18. The lid portion 12 comprises a lid portion base 12*e* and the chart 18. In the lid portion base 12*e*, a surface located on an internal space 16 side is referred to as an inner surface 12*b*, and a surface opposite to the inner surface 12*b* is referred to as an outer surface 12*a*, in the configuration of the adjustment jig 10 (see FIG. 5). The chart 18 is provided on the inner surface 12*b*. In the present embodiment, the lid portion 12 has a plate-like shape having a uniform thickness, and both sides thereof are configured in planar shapes. The shape of the lid portion base 12*e* or the lid portion 12 is not limited as long as it allows the chart 18 provided in the lid portion base 12*e* to be inclined with respect to a perpendicular plane perpendicular to the insertion direction X of the distal end part 14*a*, thereby allowing the chart 18 to be held. Therefore, the lid portion base 12*e* or the lid portion 12 may have a plate-like shape having a non-uniform thickness or may not be a plate-like shape.

Figure 7:
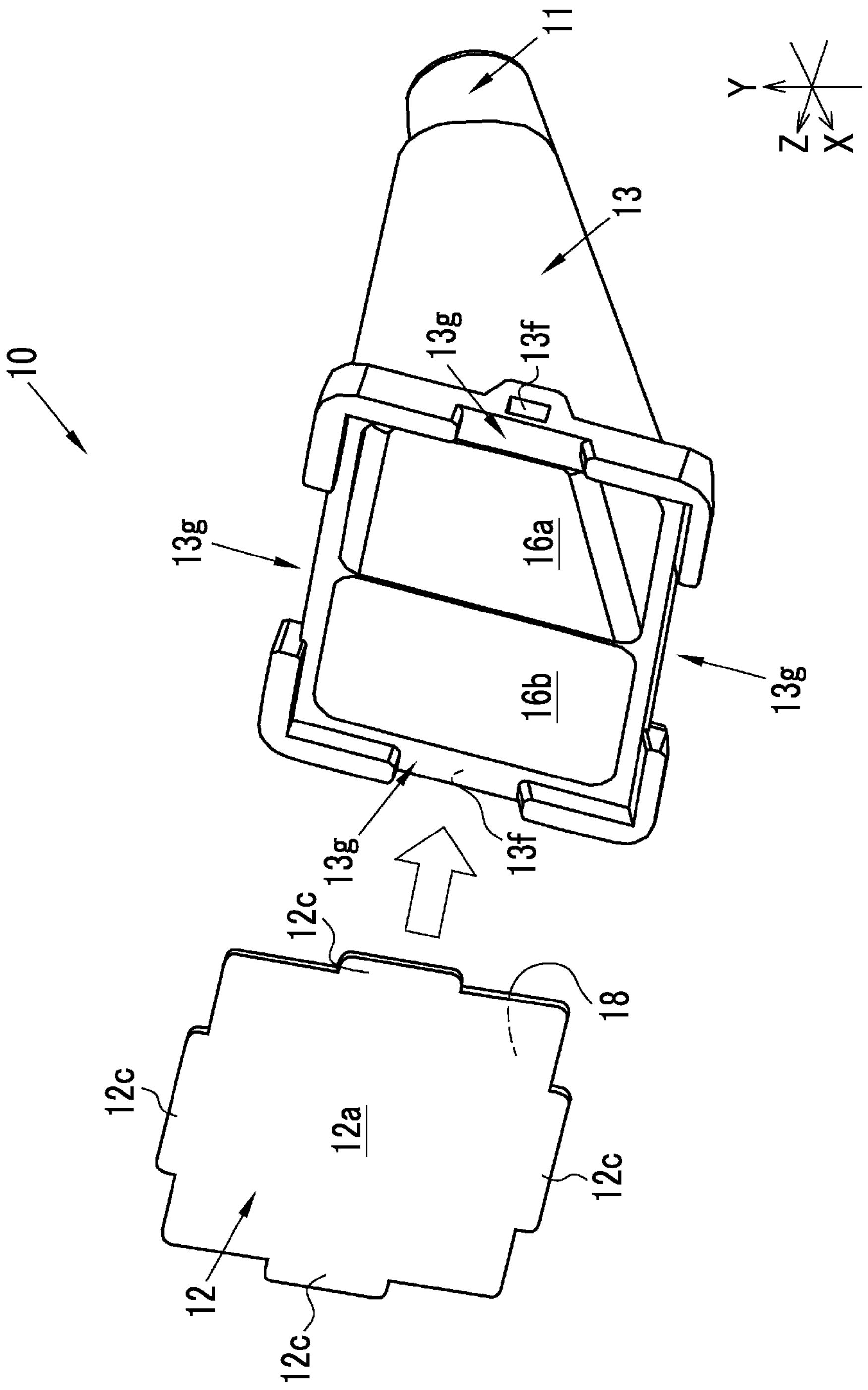
FIG. 7 is an explanatory diagram illustrating separation of the lid portion.

It is preferable that the lid portion 12 and the outer peripheral portion 13 are separably connected to each other. As shown in FIG. 7, by disconnecting the lid portion 12 and the outer peripheral portion 13, only the lid portion 12 can be removed from the adjustment jig 10. Therefore, the inside of the adjustment jig 10 can be cleaned, disinfected, and the like. In addition, only the lid portion 12 can be cleaned, replaced, and the like, and the lid portion 12 can be used by selecting a lid portion 12 provided with a chart 18 corresponding to the type of the endoscope 14 for which the white balance adjustment is desired from a plurality of the lid portions 12 and then by replacing the previously used lid portion 12. The insertion portion 11 may be inseparably integrated with the outer peripheral portion 13 or may be separably connected to the outer peripheral portion 13.

In a case where the lid portion 12 and the outer peripheral portion 13 are separable from each other, it is preferable that the lid portion 12 and the outer peripheral portion 13 are configured to be easily separated from and connected to each other. The lid portion 12 and the outer peripheral portion 13 may be separably connected to each other by magnetic force and/or fitting. That is, the lid portion 12 and the outer peripheral portion 13 may be connected to each other by using a magnet, or the lid portion 12 and the outer peripheral portion 13 may be connected to each other by fitting at least a part of each of them together through a protruding portion and a recessed portion or by using a magnet to fit at least a part of each of them together through the protruding portion and the recessed portion.

In the present embodiment, the outer peripheral portion 13 comprises a magnet insertion portion **13*f*, and a magnet (not shown) is fitted inside the magnet insertion portion 13*f* The lid portion 12 has a property that a protruding portion 12*c* corresponding to at least the magnet insertion portion 13*f* is attracted by magnetic force to a part of a recessed portion 13*g* of the outer peripheral portion 13, which corresponds to the inside of the magnet insertion portion 13*f* Therefore, the lid portion 12 and the outer peripheral portion 13 are easily connected to each other by bringing the lid portion 12 close to the outer peripheral portion 13 and are easily separated from each other by peeling off the lid portion 12 from the outer peripheral portion 13. In addition, since the protruding portion 12*c* is formed on the lid portion 12 and the recessed portion 13*g* corresponding to the protruding portion 12*c* is formed on the outer peripheral portion 13, the lid portion 12 and the outer peripheral portion 13 are easily connected to each other at appropriate positions. Therefore, the position of the chart 18 provided in the lid portion 12** can also be easily disposed at an appropriate position.

Figure 8A:
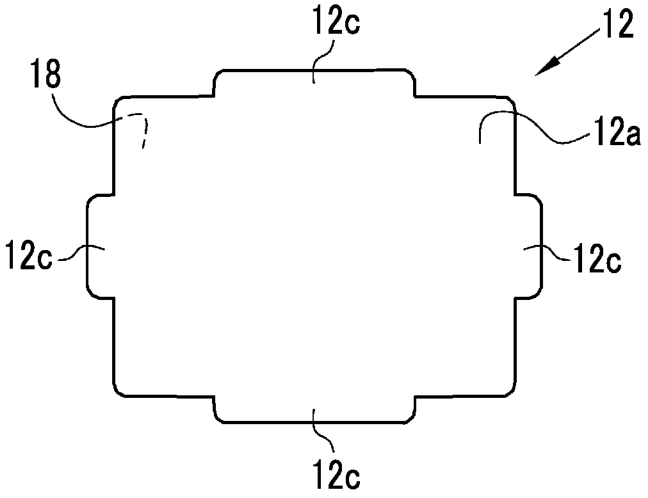
FIG. 8A is an explanatory diagram illustrating an outer surface of the lid portion.
Figure 8B:
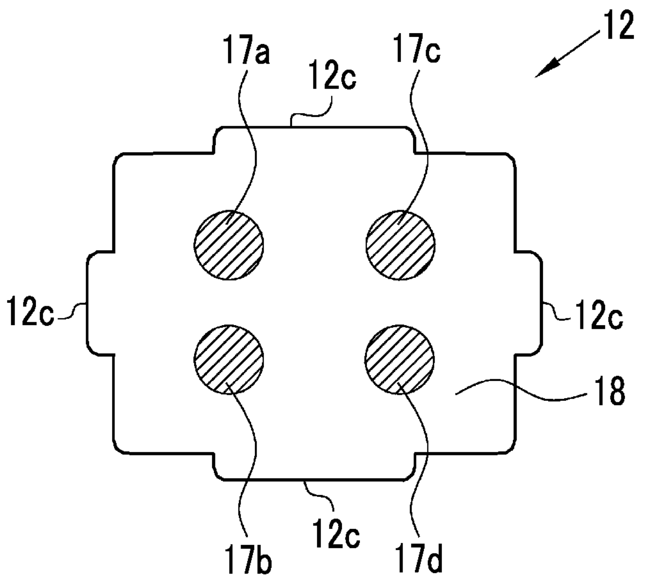
FIG. 8B is an explanatory diagram illustrating an inner surface of the lid portion.

As shown in FIG. 8A, in the separated lid portion 12, the outer surface **12*a* constitutes an outer surface of the adjustment jig 10. As shown in FIG. 8B, the chart 18 is provided in a portion of the lid portion 12, which faces the internal space 16, and a surface of the chart 18 constitutes an inner surface of the adjustment jig 10. In addition, the surface of the chart 18 has a plurality of the marks 17. The plurality of marks 17 are composed of a mark 17*a*, a mark 17*b*, a mark 17*c*, and a mark 17*d*. The marks 17 are referred to as the mark 17 in a case where these are not distinguished. The mark 17 may be formed directly on the inner surface 12*b* of the lid portion base 12*e*, or the mark 17 may be formed on a base constituting the chart 18 and the chart 18 having the mark 17 may be disposed on the inner surface 12*b*. In this case, the shape of the chart 18 may be the same as or different from that of the lid portion 12. In the present embodiment, the chart 18 has substantially the same shape as the lid portion 12 and has a rectangular shape provided with a protruding portion such as the protruding portion 12*c***.

The chart 18 is configured such that, in a case where the endoscope 14 performs the white balance adjustment, the white balance can be appropriately adjusted by imaging the chart 18. Therefore, the chart 18 and the mark 17 are configured such that the mark 17 can be imaged in an appropriate state for the white balance adjustment of the endoscope 14 in a case where the distal end part **14*a* is inserted through the insertion hole 15 and the chart 18 is imaged with an objective lens (not shown) provided in the distal end surface 14*b* of the distal end part 14*a*. The objective lens is a part that constitutes an imaging optical system of the endoscope 14**.

The chart 18 is disposed to be inclined with respect to the perpendicular plane perpendicular to the insertion direction X of the distal end part **14*a*. The perpendicular plane is a virtual plane. As a result, it is possible to appropriately image the chart 18 in a case where the white balance adjustment is performed for each of the plurality of types of endoscopes 14, which makes it possible to appropriately adjust the white balance. The plurality of types of endoscopes 14 used herein are types that are distinguished by angles in an optical axis direction of the imaging optical system with respect to an axial direction of the distal end part 14*a***.

Examples of the plurality of types of endoscopes 14 include a direct-viewing endoscope in which the optical axis direction of the imaging optical system is parallel to the axial direction of the distal end part **14*a*, and an oblique-viewing endoscope in which the optical axis direction of the imaging optical system has an angle with respect to the axial direction of the distal end part 14*a*. In a case where the endoscope 14 is a rigid endoscope and has a linear scope, the axial direction of the distal end part 14*a* is the same as the axial direction of the scope. In a case where the endoscope 14 is a flexible endoscope but the distal end part 14*a* has a scope that does not bend, the types of the endoscope 14 can be distinguished based on the optical axis direction of the imaging optical system with respect to the axial direction of the distal end part 14*a***. The oblique-viewing endoscope may be called a side-viewing endoscope or the like.

Figure 9A:
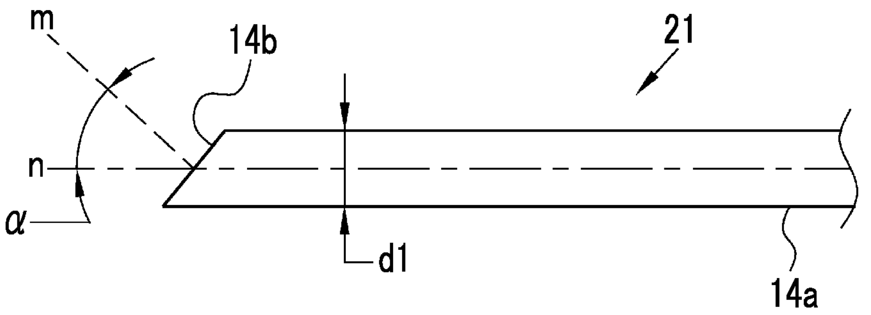
FIG. 9A is an explanatory diagram illustrating an oblique-viewing endoscope.
Figure 9B:
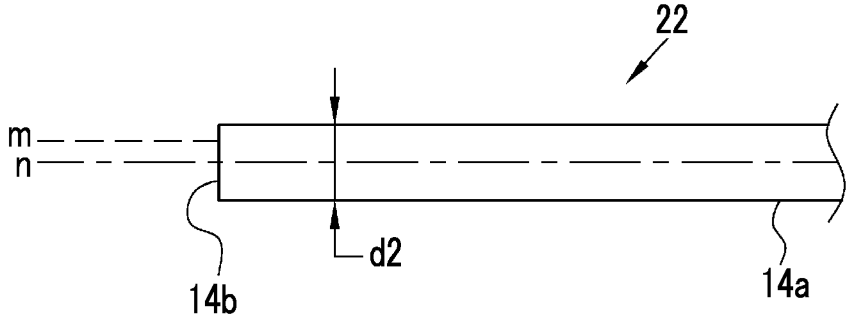
FIG. 9B is an explanatory diagram illustrating a direct-viewing endoscope.

As shown in FIG. 9A, in an oblique-viewing endoscope 21, an oblique angle $\alpha$, which is an angle formed by an optical axis direction m of the imaging optical system and an axial direction n of the distal end part **14*a*, is, for example, 30 degrees, 45 degrees, or the like. As shown in FIG. 9B, in a direct-viewing endoscope 22, the optical axis direction m of the imaging optical system is parallel to the axial direction n of the distal end part 14*a*. The direct-viewing endoscope 22 can obtain an endoscope image of a subject that is located forward of the distal end part 14*a* in the axial direction, and the oblique-viewing endoscope 21 can obtain an endoscope image of a subject that is located forward of a slightly angled side surface when viewed from the axial direction of the distal end part 14*a*. In a case of the direct-viewing endoscope 22 in which the optical axis direction m of the imaging optical system is parallel to the axial direction n of the distal end part 14*a***, it can be said that the oblique angle $\alpha$ is 0 degrees.

In the adjustment jig 10, by disposing the chart 18, on which the mark 17 is appropriately disposed, to be inclined to an appropriate degree with respect to the perpendicular plane perpendicular to the insertion direction X, the distance and the angle between the mark 17 and the distal end surface **14*b* of the endoscope comprising the objective lens are within predetermined ranges in a case where the mark 17 is imaged, in any of the plurality of types of endoscopes 14 having various oblique angles $\alpha$, including a case of the direct-viewing endoscope 22 in which the oblique angle α is 0 degrees. Therefore, in a case where the endoscope image obtained by imaging the chart 18** is used to adjust the white balance, it is possible to appropriately adjust the white balance.

The degree of inclination of the chart 18 need only be decided on such that, in a case where the endoscope image obtained by imaging the chart 18 with each of the plurality of endoscopes 14 is used for the white balance adjustment, the distance and the angle between the distal end surface 14*b* and the mark 17 are within predetermined ranges and the color, the brightness, the distortion, and the like of the mark 17 caused by the inclination of the chart 18 do not pose a problem for the white balance adjustment. The degree of inclination of the chart 18 can be indicated by the inclination of the chart 18 with respect to a perpendicular plane perpendicular to the optical axis of the direct-viewing endoscope or the oblique-viewing endoscope. The angle of inclination of the chart 18 is an angle in a case where a lower part of the chart 18 is used as an axis when the adjustment jig 10 is used. That is, the angle is an angle in a state in which the bottom surface part 13*b* of the adjustment jig 10 is located downward because the bottom surface part 13*b* of the outer peripheral portion 13 is disposed vertically downward when the adjustment jig 10 is used. Further, it is assumed that the angle of inclination is positive in a case where the chart 18 is inclined toward an insertion portion 11 side and the angle of inclination is negative in a case where the chart 18 is inclined toward a side opposite to the insertion portion 11.

Figure 10:
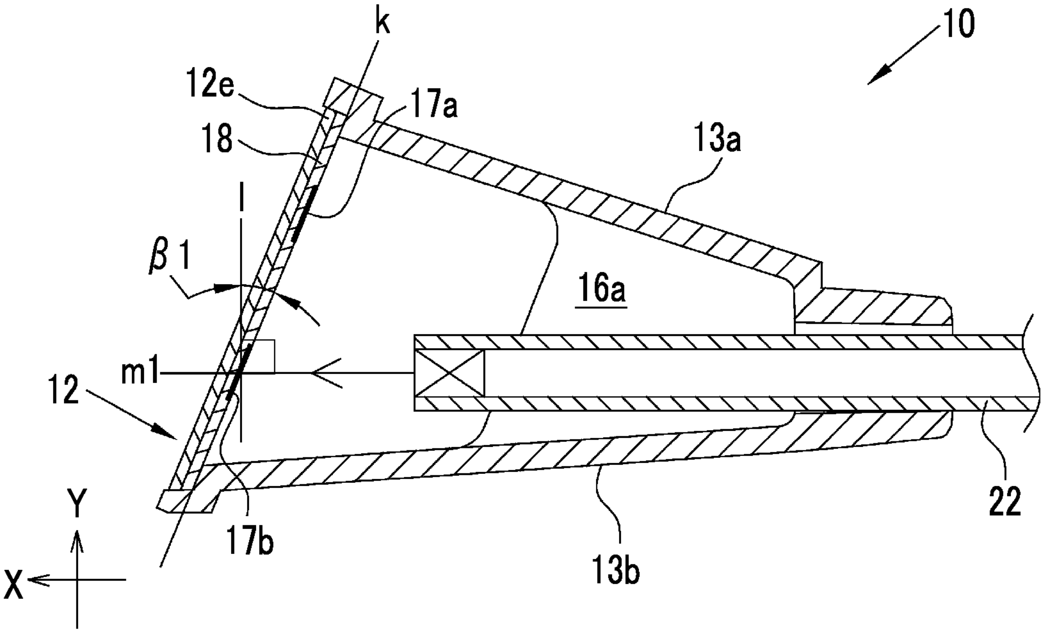
FIG. 10 is a cross-sectional view cut along the line I-I of FIG. 4 and is an explanatory diagram illustrating an inclination angle in a case where the direct-viewing endoscope is used.
Figure 11:
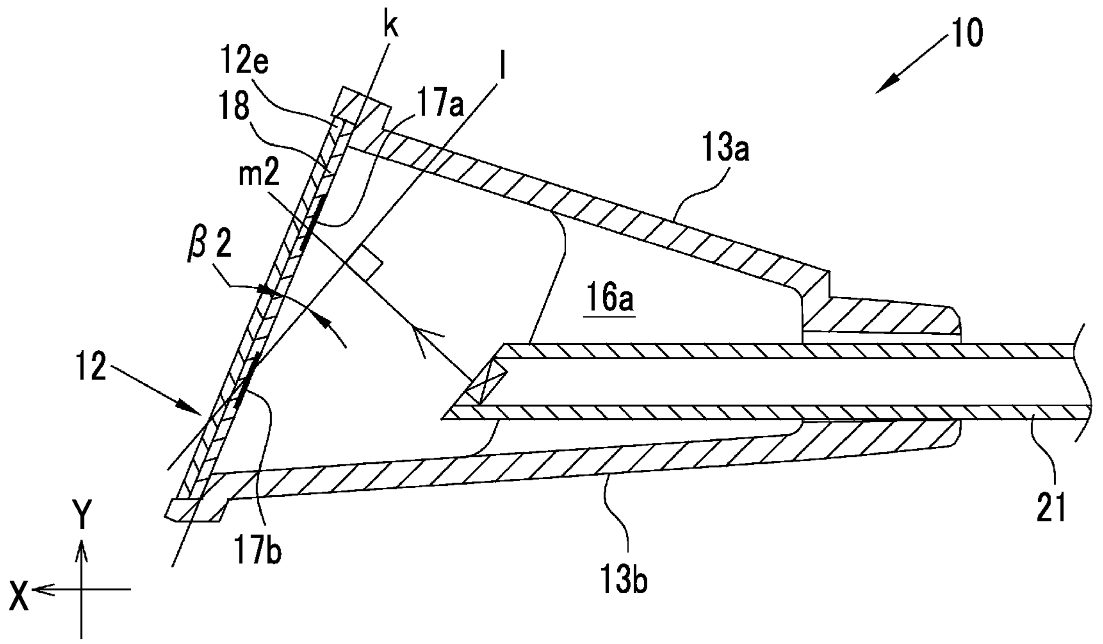
FIG. 11 is a cross-sectional view cut along the line I-I of FIG. 4 and is an explanatory diagram illustrating an inclination angle in a case where the oblique-viewing endoscope is used.

As shown in FIG. 10, in the direct-viewing endoscope 22, a surface k of the chart 18 is disposed to have an inclination angle (31 with respect to a perpendicular plane 1 perpendicular to an optical axis direction m1 of the imaging optical system of the direct-viewing endoscope 22. Since the optical axis direction m1 of the direct-viewing endoscope 22 is the same as the insertion direction, the perpendicular plane 1 perpendicular to the optical axis direction m1 of the direct-viewing endoscope 22 can be a perpendicular plane perpendicular to the insertion direction. Further, as shown in FIG. 11, in the oblique-viewing endoscope 21, the surface k of the chart 18 is disposed to have an inclination angle (32 with respect to a perpendicular plane 1 perpendicular to an optical axis direction m2 of the imaging optical system of the oblique-viewing endoscope 21. In some parts of the figure, in order to prevent the figure from becoming complicated, hatching or the like showing a cross-section may be omitted.

The inclination angle (31 or the inclination angle (32 is an angle at which the mark 17 can be appropriately imaged to enable appropriate white balance adjustment, in a case where the white balance adjustment is performed by obtaining the endoscope image obtained by imaging the chart 18 with the direct-viewing endoscope 22. With the inclination angle (31, the direct-viewing endoscope 22 appropriately images the mark 17*b*. Similarly, with the inclination angle (32, the oblique-viewing endoscope 21 appropriately images the mark 17*a*. The inclination angle (31 and the inclination angle (32 have angle ranges in which the oblique-viewing endoscope 21 and the direct-viewing endoscope 22 can appropriately perform the white balance adjustment. Therefore, the inclination of the chart 18 with respect to the perpendicular plane perpendicular to the insertion direction can be set to satisfy both the inclination angle (31 and the inclination angle (32.

Figure 12:
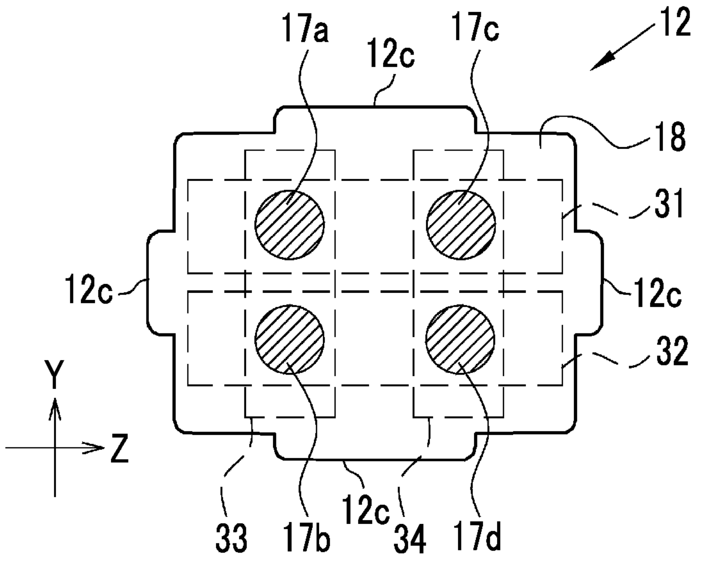
FIG. 12 is an explanatory diagram illustrating disposition of a plurality of marks.

As shown in FIG. 12, the chart 18 has four marks 17*a*, 17*b*, 17*c*, and 17*d* that are disposed such that two marks are arranged vertically (in a vertical direction Y) and two marks are arranged horizontally (in a width direction Z). The four marks 17*a*, 17*b*, 17*c*, and 17*d* are all circular in shape and are disposed upward, downward, leftward, rightward on the chart 18. The marks 17*a* and 17*b* are disposed on the left side facing toward the paper surface in FIG. 12 and are imaged in a case where the distal end part 14*a* is inserted through the first insertion hole 15*a*. The marks 17*c* and 17*d* are imaged in a case where the distal end part 14*a* is inserted through the second insertion hole 15*b*.

Further, in a case where a region 31 consisting of the mark 17*a* or the mark 17*c* is above a region 32 consisting of the mark 17*b* or the mark 17*d* in the vertical direction Y, the direct-viewing endoscope 22 images the mark 17 included in the region 32 consisting of the mark 17*b* or the mark 17*d*, and the oblique-viewing endoscope 21 images the mark 17 included in the region 31 consisting of the mark 17*a* or the mark 17*c*. Further, the marks 17*a* and 17*b* included in the region 33 are imaged by the direct-viewing endoscope 22 or the oblique-viewing endoscope 21 having an outer diameter of up to 10 mm, and the marks 17*c* and 17*d* included in a region 34 are imaged by the direct-viewing endoscope 22 or the oblique-viewing endoscope 21 having an outer diameter of up to 5 mm. Therefore, in this case, in a case where the oblique-viewing endoscope 21 is inserted into the insertion hole 15, the oblique-viewing endoscope 21 is inserted such that the optical axis direction m2 faces a vertically upward direction.

In the present embodiment, since the inner diameter of the inlet of the first insertion hole 15*a* is 11 mm and the inner diameter of the inlet of the second insertion hole 15*b* is 6 mm, the direct-viewing endoscope 22 in which the distal end part 14*a* inserted through the first insertion hole 15*a* has an outer diameter of 10 mm images the mark 17*b* and the oblique-viewing endoscope 21 in which the distal end part 14*a* has an outer diameter of 10 mm images the mark 17*a*. In addition, the direct-viewing endoscope 22 in which the distal end part 14*a* inserted through the second insertion hole 15*b* has an outer diameter of 5 mm images the mark 17*d*, and the oblique-viewing endoscope 21 in which the distal end part 14*a* has an outer diameter of 5 mm images the mark 17*c*.

As described above, by inclining the chart 18, the white balance adjustment can be appropriately performed regardless of whether the type of the endoscope 14 is the oblique-viewing endoscope 21 or the direct-viewing endoscope 22. In the present embodiment, the chart 18 is inclined toward the insertion portion side with the lower part of the chart 18 as an axis. Further, as described above, in a case where the plurality of insertion holes 15 are provided according to the diameter of the endoscope, the white balance adjustment can be performed regardless of whether the type of the endoscope 14 is the large diameter endoscope 14*c* or the small diameter endoscope 14*d*.

That is, since the adjustment jig 10 is configured as described above such that the chart 18 is inclined with respect to the perpendicular plane perpendicular to the insertion direction, appropriate white balance adjustment can be performed for any of four types of the endoscopes 14, that is, the large diameter endoscope 14*c* as the oblique-viewing endoscope 21, the small diameter endoscope 14*d* as the oblique-viewing endoscope 21, the large diameter endoscope 14*c* as the direct-viewing endoscope 22, and the small diameter endoscope 14*d* as the direct-viewing endoscope 22.

In the chart 18, by providing, on the chart 18, the number of marks 17 obtained by multiplying the number of insertion holes 15 with the number of types of oblique angles α formed by the optical axis direction m of the imaging optical system and the axial direction n of the distal end part 14*a*, the adjustment jig 10 can perform appropriate white balance adjustment for any of the types of endoscopes 14, which correspond to the number of marks 17 provided in the adjustment jig 10.

As described above, the number of insertion holes 15 is not limited to two. For example, in a case where three insertion holes 15 are installed according to the diameters of the endoscopes, that is, the large diameter endoscope 14*c*, a medium diameter endoscope that is appropriate for the endoscope 14 having an intermediate diameter between the large diameter and the small diameter, and the small diameter endoscope 14*d*, two types, that is, the oblique-viewing endoscope 21 and the direct-viewing endoscope 22, can be employed for each of the diameters. In this case, by setting six marks 17 on the chart 18, appropriate white balance adjustment can be performed for any of six types of endoscopes 14.

Figure 13:
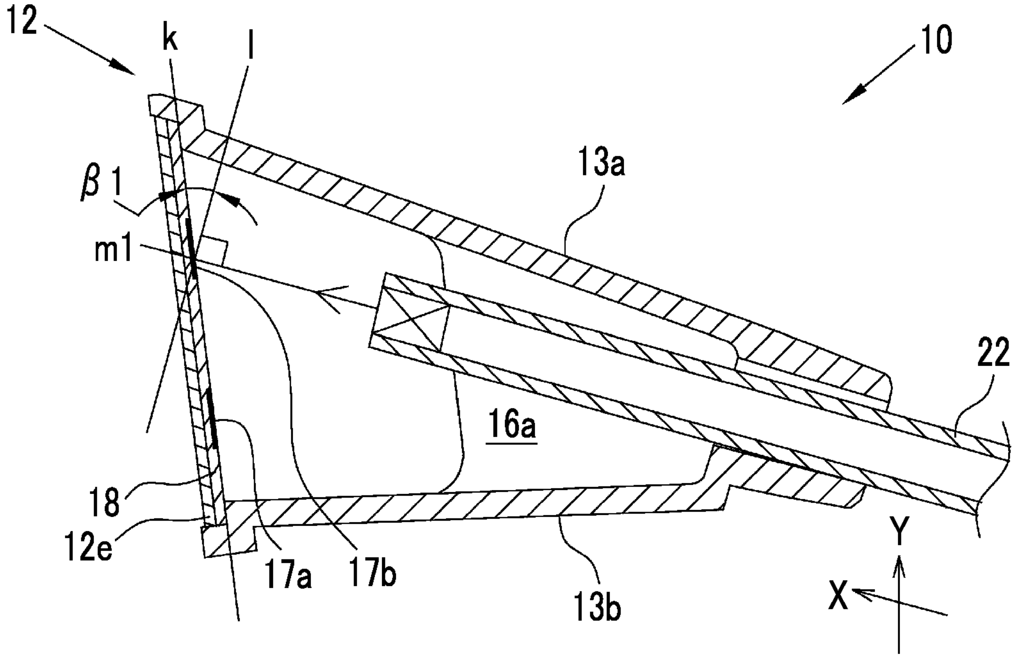
FIG. 13 is a cross-sectional view of an adjustment jig of another example and is an explanatory diagram illustrating an inclination angle in a case where the direct-viewing endoscope is used.
Figure 14:
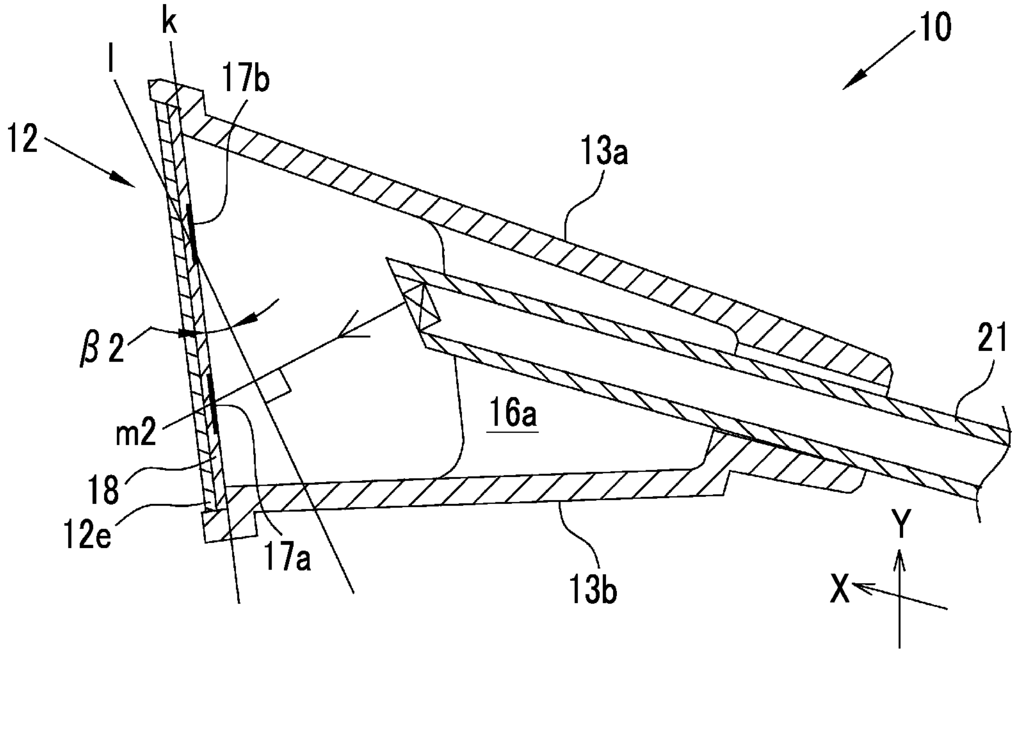
FIG. 14 is a cross-sectional view of an adjustment jig of another example and is an explanatory diagram illustrating an inclination angle in a case where the oblique-viewing endoscope is used.

The chart 18 may be inclined toward a side opposite to the insertion portion side. As shown in FIG. 13, in this case, the direct-viewing endoscope 22 images the mark 17*a* disposed at the upper part of the chart 18. Since the optical axis direction m1 of the direct-viewing endoscope 22 is the same as the insertion direction, the perpendicular plane 1 perpendicular to the optical axis direction m1 of the direct-viewing endoscope 22 can be a perpendicular plane perpendicular to the insertion direction. Further, as shown in FIG. 14, the oblique-viewing endoscope 21 images the mark 17*b* disposed at the lower part of the chart 18. As described above, by disposing the chart 18, on which the corresponding marks 17 are disposed, to be inclined with respect to the perpendicular plane perpendicular to the insertion direction, the mark 17 can be appropriately imaged by any of the direct-viewing endoscope 22 or the oblique-viewing endoscope 21. In addition, the shape of the insertion hole 15, the disposition of the marks 17, and the like may be used to prevent an inappropriate mark 17 for the inserted endoscope 14 from being shown.

The color, the shape, the disposition, and the like of the mark 17 provided in the chart 18 are set in advance according to the type of the endoscope 14 for which the white balance adjustment is performed. Therefore, it is preferable that the mark has a reference color suitable for adjusting the white balance in each endoscope 14. The reference color is a color for creating white in the endoscope image. In the chart 18, it is preferable that a portion other than the mark 17 has a color that allows for easy recognition of the mark 17. For example, in the chart 18, it is preferable that a portion other than the mark 17 has a color different from that of the mark 17 such that the mark 17 is easily identified.

In addition, it is preferable that the mark 17 has a shape such that the shape of the mark 17 is easily grasped in a case where the mark 17 is imaged in a state in which the white balance adjustment of the endoscope 14 is appropriate, that is, in a state in which the distance between the distal end surface 14*b* and the chart 18 is appropriate. For example, the shape of the mark 17 may be a shape that is easily recognizable, such as a circle, an ellipse, a triangle, a quadrangle, or a polygon. The shape also includes the size of the mark 17. In addition, the shape need only be a shape with which the white balance can be appropriately adjusted, and may be a filled shape or a shape of an unfilled contour having a certain width.

Since the mark 17 has a specific shape, the user can view a display 55 on which the endoscope image is displayed in a case where the distal end part 14*a* is inserted into the insertion hole 15 and the chart 18 is imaged, thereby using the shape or the contour of the mark 17 to determine whether or not the mark 17 is imaged in an appropriate state. The user can adjust the distance between the distal end surface 14*b* and the chart 18 such that the shape or the contour of the mark 17 is appropriate.

In this manner, in a case where the distance between the distal end surface 14*b* and the chart 18 or the like is appropriate, the white balance adjustment may be performed on a video as it is, or a still image may be acquired and then the white balance adjustment may be performed using this still image. The chart 18 has at least two marks 17.

Figure 15:
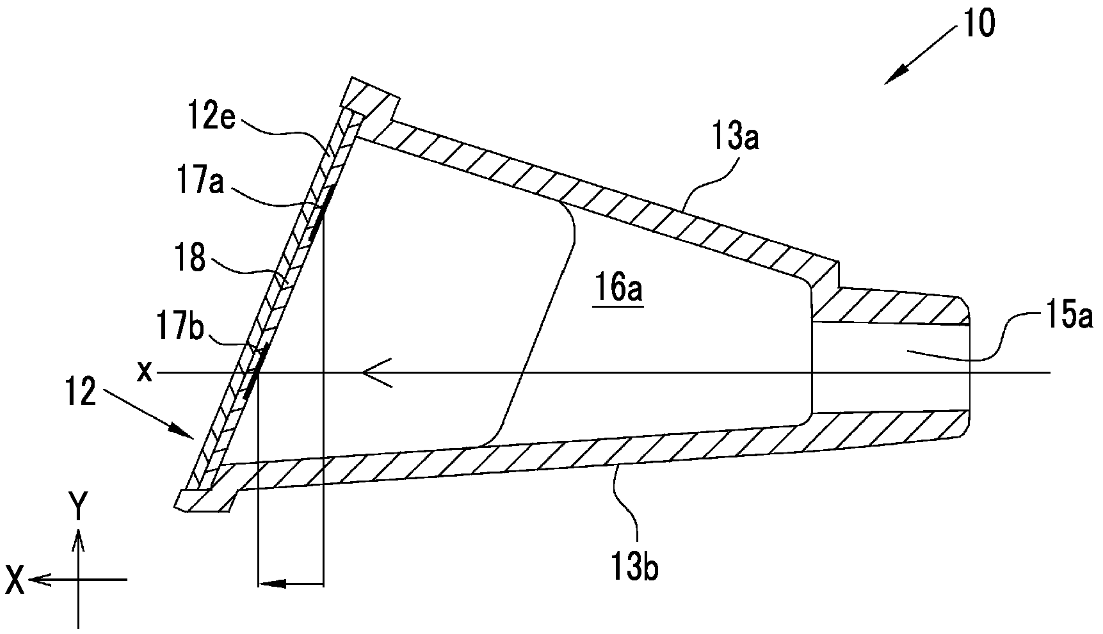
FIG. 15 is a cross-sectional view cut along the line I-I of FIG. 4 and is an explanatory diagram illustrating disposition of the marks.

It is preferable that the plurality of marks 17 are disposed in the chart 18 along the insertion direction X of the distal end part 14*a*. As shown in FIG. 15, since the chart 18 is inclined with respect to the perpendicular plane 1 perpendicular to the insertion direction X, the plurality of marks 17 disposed in the chart 18 along the insertion direction X of the endoscope 14 to be inserted into the first insertion hole 15*a* are the mark 17*a* and the mark 17*b* disposed in the region 33 (see FIG. 12). Similarly, the plurality of marks 17 disposed along the insertion direction X of the endoscope 14 to be inserted into the second insertion hole 15*b* are the mark 17*c* and the mark 17*d* disposed in the region 34 (see FIG. 12). By disposing the plurality of marks 17 along the insertion direction X, the mark 17 can also be appropriately imaged using any of the direct-viewing endoscope 22 or the oblique-viewing endoscope 21 in a case where the same insertion hole 15 is used.

Figure 16:
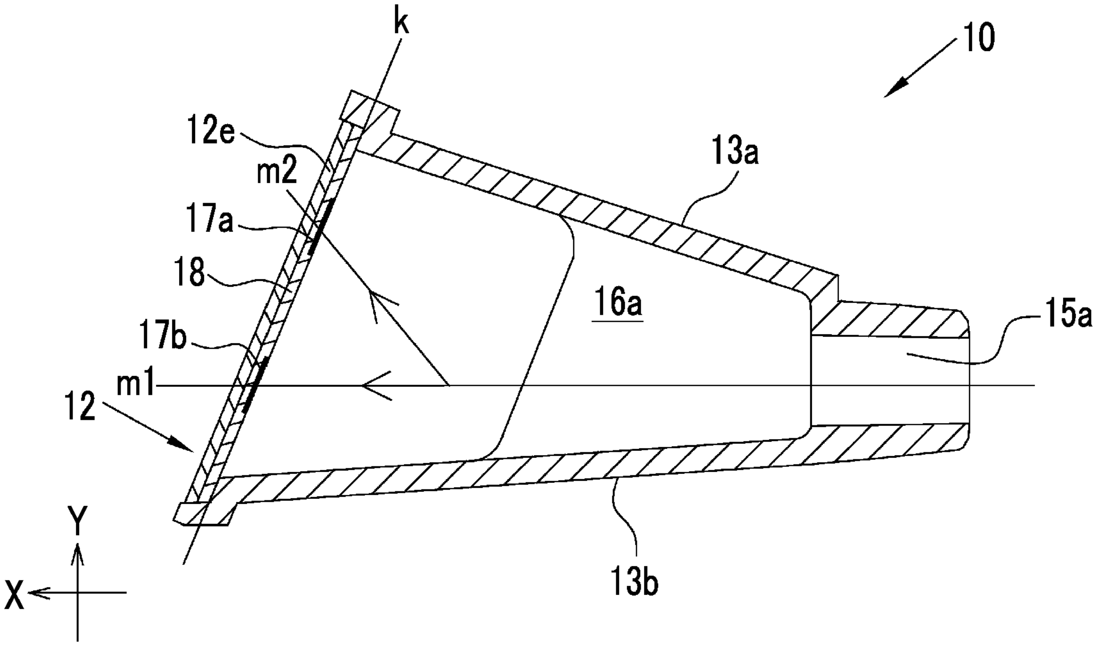
FIG. 16 is a cross-sectional view cut along the line I-I of FIG. 4 and is an explanatory diagram illustrating the insertion hole and the disposition of the marks.

As shown in FIG. 16, it is preferable that one of the plurality of marks 17 is disposed at a position where the chart 18 and the optical axis direction m of the endoscope 14 to be inserted into the insertion hole 15 intersect with each other. In FIG. 16, the mark 17*b* is disposed in correspondence with the first insertion hole 15*a*. The mark 17*b* is disposed at a position where the surface k of the chart 18 and the optical axis direction m1 of the direct-viewing endoscope 22 to be inserted into the first insertion hole 15*a* intersect with each other. Similarly, the mark 17*a* is disposed in correspondence with the first insertion hole 15*a*. The mark 17*a* is disposed at a position where the surface k of the chart 18 and the optical axis direction m2 of the oblique-viewing endoscope 21 to be inserted into the first insertion hole 15*a* intersect with each other. In addition, similarly, the mark 17*d* and the mark 17*c* are disposed in correspondence with the second insertion hole 15*b*. The mark 17*d* is disposed at a position where the surface k of the chart 18 and the optical axis direction m1 of the direct-viewing endoscope 22 to be inserted into the second insertion hole 15*b* intersect with each other, and the mark 17*c* is disposed at a position where the surface k of the chart 18 and the optical axis direction m2 of the oblique-viewing endoscope 21 to be inserted into the second insertion hole 15*b* intersect with each other. As a result, an endoscope image obtained by appropriately imaging the mark 17 for performing the white balance adjustment can be obtained even in a case of using any of the direct-viewing endoscope 22 or the oblique-viewing endoscope 21 and a case of inserting the endoscope into any of the plurality of insertion holes 15.

As described above, since the chart 18 is moderately inclined with respect to the perpendicular plane 1 perpendicular to the optical axis direction m regardless of whether the type of the endoscope 14 is the direct-viewing endoscope 22 or the oblique-viewing endoscope 21, the mark 17 can be appropriately imaged by setting the angle between the optical axis direction m of each of the endoscopes 14 and the chart 18 to be within a range in which a problem does not occur for the white balance adjustment. Therefore, the endoscope 14 having the distal end part 14*a* to be inserted into the insertion hole 15 may be the direct-viewing endoscope 22 or the oblique-viewing endoscope 21.

In addition, it is preferable that the distal end part 14*a* to be inserted into the adjustment jig 10 does not bend. Therefore, it is preferable that the endoscope 14 having the distal end part 14*a* to be inserted into the insertion hole 15 is a rigid endoscope. In a case where the endoscope 14 is a flexible endoscope, it is preferable that the distal end part 14*a* has at least a scope that does not bend.

Here, specific examples of the inclination angle β1 and the inclination angle β2 will be described. The inclination angle θ1 and the inclination angle θ2 may be decided on based on measured values using the plurality of types of endoscopes 14 including the direct-viewing endoscope 22 and the oblique-viewing endoscope 21. A device similar to the adjustment jig 10 was used to perform the white balance adjustment based on the endoscope image captured at the inclination angle β1 or the inclination angle β2 as an angle set in advance for the plurality of types of rigid endoscopes 14, including the direct-viewing endoscope 22 and the oblique-viewing endoscope 21, and the signal ratio deviation in the endoscope image was actually measured. Specifically, the signal ratio deviation actually measured for the plurality of types of endoscopes 14 including the direct-viewing endoscope 22 and the oblique-viewing endoscope 21 was represented by a percentage, the inclination angle (3 and the signal ratio deviation were plotted on a graph 35 by averaging measured values in the plurality of endoscopes 14, and a range R1 and a range R2 in which the signal ratio deviation does not pose a problem for white balance adjustment were decided on. The signal ratio deviation is used to represent a case where achromatic color is obtained by averaging pixels of each color in the entire obtained endoscope image as a value of 0%, and a case where the maximum colorfulness is obtained by averaging pixels of each color as a value of 100%. In the graph 35, the vertical axis represents the signal ratio deviation, and the horizontal axis represents the absolute value of the inclination angle β. The inclination angle β1 and the inclination angle β2 are referred to as the inclination angle β in a case where these are not distinguished.

Figure 17:
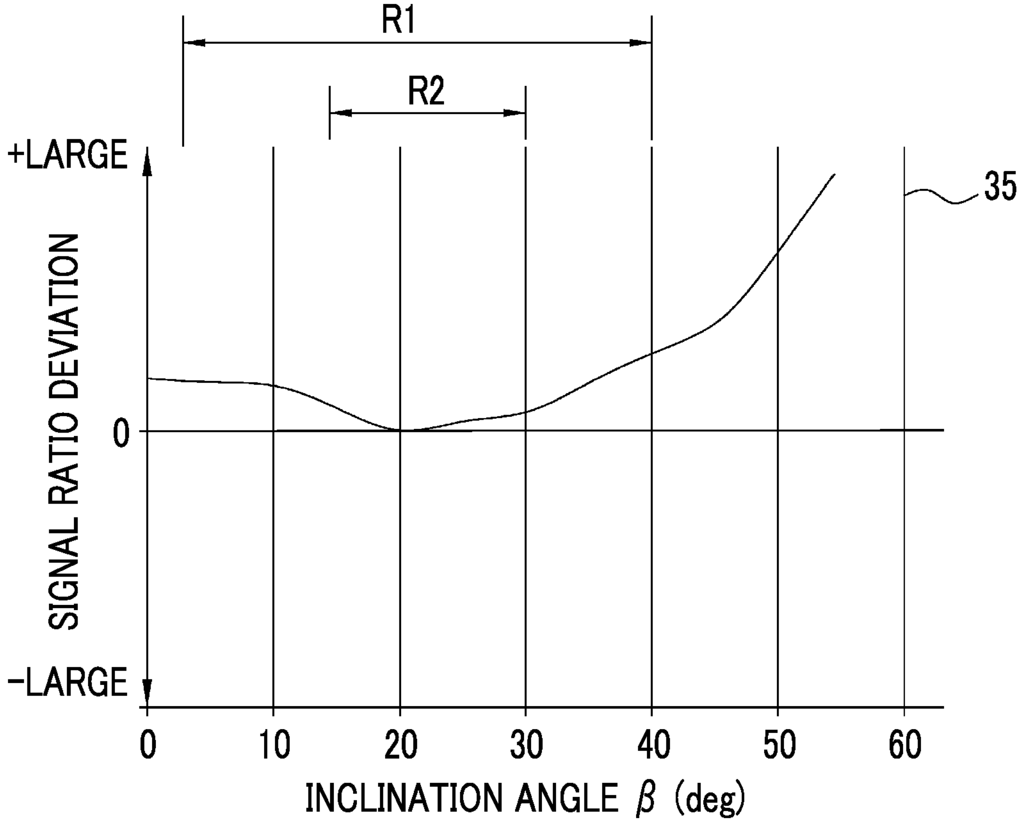
FIG. 17 is a graph showing a relationship between an inclination angle R and a signal ratio deviation.

As shown in FIG. 17, from the graph 35, the inclination angle β is preferably in the range R1 and more preferably in the range R2 because the signal ratio deviation is small and there is no problem in the white balance adjustment. Therefore, the inclination angle β1 in the direct-viewing endoscope 22 is preferably within 40 degrees and more preferably within 30 degrees. In addition, in a case where the insertion portion 11 side is defined as positive, the inclination angle β2 of the oblique-viewing endoscope 21 is preferably within 40 degrees in a negative direction and a positive direction with the perpendicular plane 1 as a reference, and is more preferably within 30 degrees in the same directions. Further, the inclination angle β1 or the inclination angle β2 is preferably 5 degrees or more. The inclination angle β1 is not set to 0 degrees. Further, it is more preferable that the inclination angle β1 or the inclination angle β2 is 15 degrees or more according to the range R2 of the graph 35.

From the above, in a case where the endoscope is the direct-viewing endoscope 22, the chart 18 is preferably inclined at the inclination angle β1 within a range of 5 degrees or more and 40 degrees or less and more preferably inclined at the inclination angle β1 within a range of 15 degrees or more and 30 degrees or less, with respect to the perpendicular plane perpendicular to the optical axis of the endoscope in a case where the inclination toward the insertion portion 11 side is defined as positive with the lower part of the chart 18 of the adjustment jig 10 in use as an axis. Similarly, in a case where the endoscope is the oblique-viewing endoscope 21, the chart 18 is preferably inclined at the inclination angle β2 within a range of −40 degrees or more and 40 degrees or less and more preferably inclined at the inclination angle β2 within a range of −30 degrees or more and 30 degrees or less, with respect to the perpendicular plane perpendicular to the optical axis of the endoscope in a case where the inclination toward the insertion portion 11 side is defined as positive with the lower part of the chart 18 of the adjustment jig 10 in use as an axis. Further, by setting the inclination angle β1 and the inclination angle β2 as described above, it is possible to capture an appropriate endoscope image for the white balance adjustment in the direct-viewing endoscope 22 or the oblique-viewing endoscope 21.

In a case of a right-handed user, the adjustment jig 10 of the present embodiment may be often used in such a manner that, for example, the bottom surface part 13*b* is placed on the left hand, the adjustment jig 10 is gripped by the left hand, the endoscope 14 is held by the right hand, and the distal end part 14*a* of the endoscope is inserted into the insertion hole 15. In a case where the adjustment jig 10 is used in such an aspect, the configuration of the chart may depend on the shape of the adjustment jig 10, the insertion direction, the usage method of the adjustment jig 10, and the like, but it is preferable that the chart 18 is inclined toward the insertion portion 11 side with the lower part of the chart 18 as an axis (see FIGS. 10 and 11). In this case, the angle described above is an angle in a case where the insertion portion 11 side is defined as positive. By inclining the chart 18 toward the insertion portion 11 side, it is possible to appropriately and stably perform imaging in an appropriate aspect for the white balance adjustment in both the direct-viewing endoscope 22 and the oblique-viewing endoscope 21, such as a case of using the adjustment jig 10 in such a manner that the bottom surface part 13*b* is placed on the left hand, the adjustment jig 10 is gripped by the left hand, the endoscope 14 is held by the right hand, and the distal end part 14*a* of the endoscope is inserted into the insertion hole 15, as described above.

As the form of the adjustment jig 10, not only a form for using the bottom surface part 13*b* as the lower part as in the present embodiment (see FIG. 1), but also a shape may be employed in which the left side surface part 13*d* is positioned at the lowest and the chart 18 is inclined toward the insertion portion 11 side with the right part of the chart 18 as an axis. Similarly, a shape may be employed in which the right side surface part 13*c* is positioned at the lowest and the chart 18 is inclined toward the insertion portion 11 side with the left part of the chart 18 as an axis. That is, even in a case of the adjustment jig in which the adjustment jig 10 of the present embodiment is rotated in the width direction Z, the chart 18 need only be inclined with respect to the perpendicular plane perpendicular to the insertion direction with any portion of the chart 18 as an axis.

Figure 18:
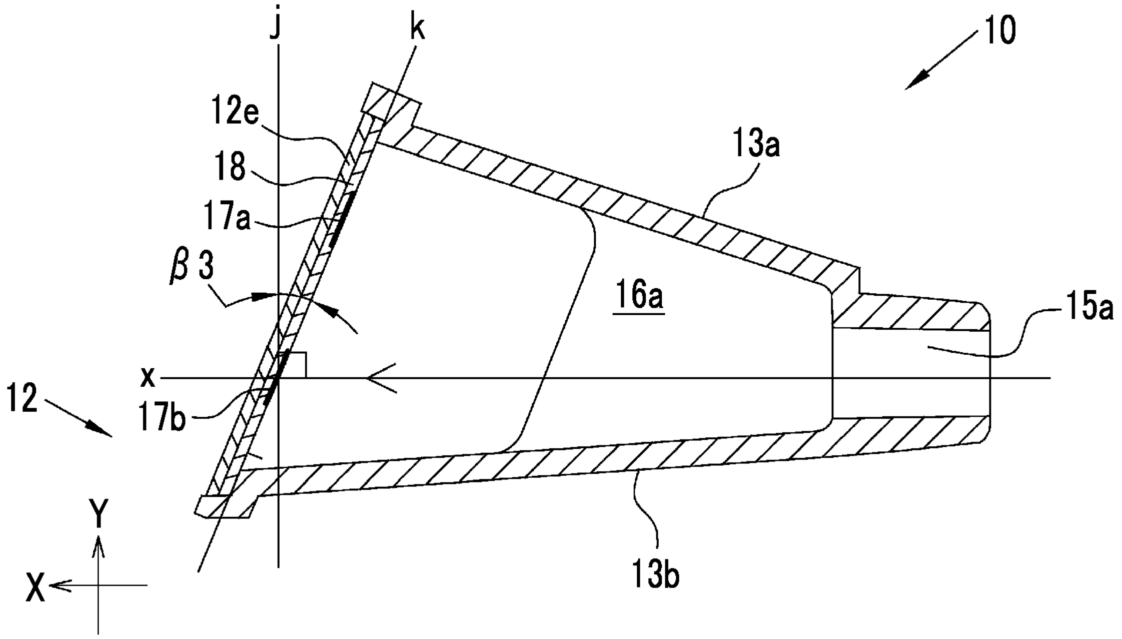
FIG. 18 is a cross-sectional view cut along the line I-I of FIG. 4 and is an explanatory diagram illustrating an inclination angle of a surface of the chart with respect to a perpendicular plane j perpendicular to an insertion direction of the distal end part.

Further, using a preferable range of the inclination angle β1 in the direct-viewing endoscope 22 and the inclination angle β2 in the oblique-viewing endoscope 21, as shown in FIG. 18, the degree of inclination of the chart 18 may be indicated by an inclination angle β3 of the surface k of the chart 18 with respect to a perpendicular plane j perpendicular to the insertion direction X of the distal end part 14*a*. In a case where the oblique angle α of the oblique-viewing endoscope 21 is assumed to be 45 degrees at the maximum, in order to perform appropriate white balance adjustment in the direct-viewing endoscope 22 and the oblique-viewing endoscope 21 having an oblique angle α of up to 45 degrees, a lower limit of the inclination angle β3 is preferably 5 degrees or more and more preferably 15 degrees or more. In addition, an upper limit of the inclination angle β3 is preferably 40 degrees or less and more preferably 30 degrees or less.

By setting the inclination angle β3 to be within a range of 5 degrees or more and 40 degrees or less, both the inclination angle β1 and the inclination angle β2 can be satisfied in the direct-viewing endoscope 22 and the oblique-viewing endoscope 21 having an oblique angle α of up to 45 degrees, and appropriate white balance adjustment can be performed for any of the direct-viewing endoscope 22 and the oblique-viewing endoscopes 21 having various oblique angles α. By setting the inclination angle β3 to be within a range of 15 degrees or more and 30 degrees or less, appropriate white balance adjustment can be more reliably performed for any of the direct-viewing endoscope 22 and the oblique-viewing endoscopes 21 having various oblique angles α. In the present embodiment, the inclination angle β3 is set to 25 degrees.

Figure 19:
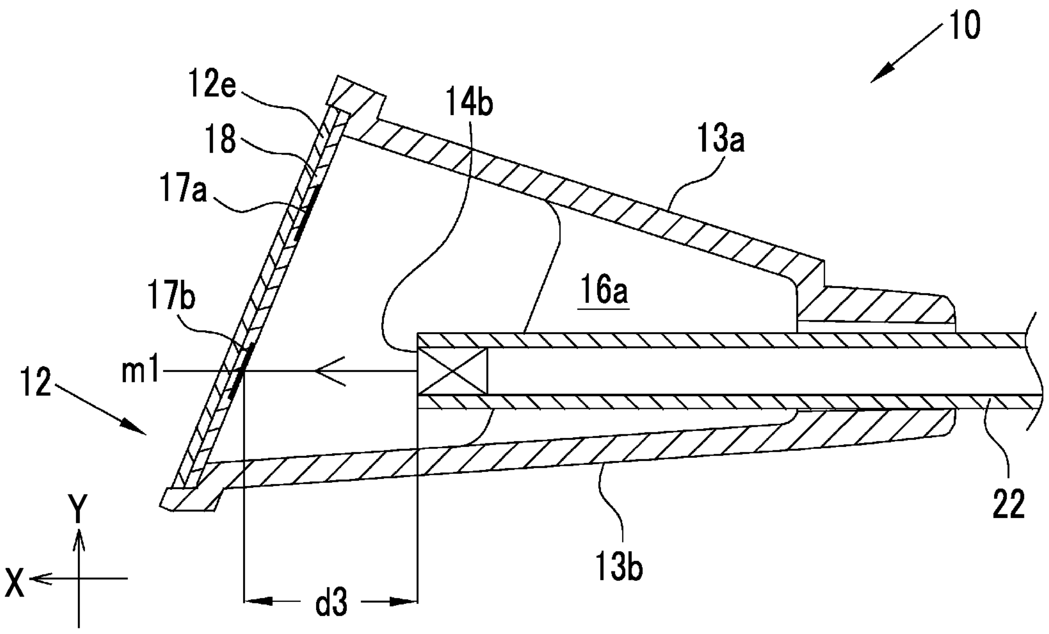
FIG. 19 is a cross-sectional view cut along the line I-I of FIG. 4 and is an explanatory diagram illustrating a distance between a distal end surface in the direct-viewing endoscope and the chart.
Figure 20:
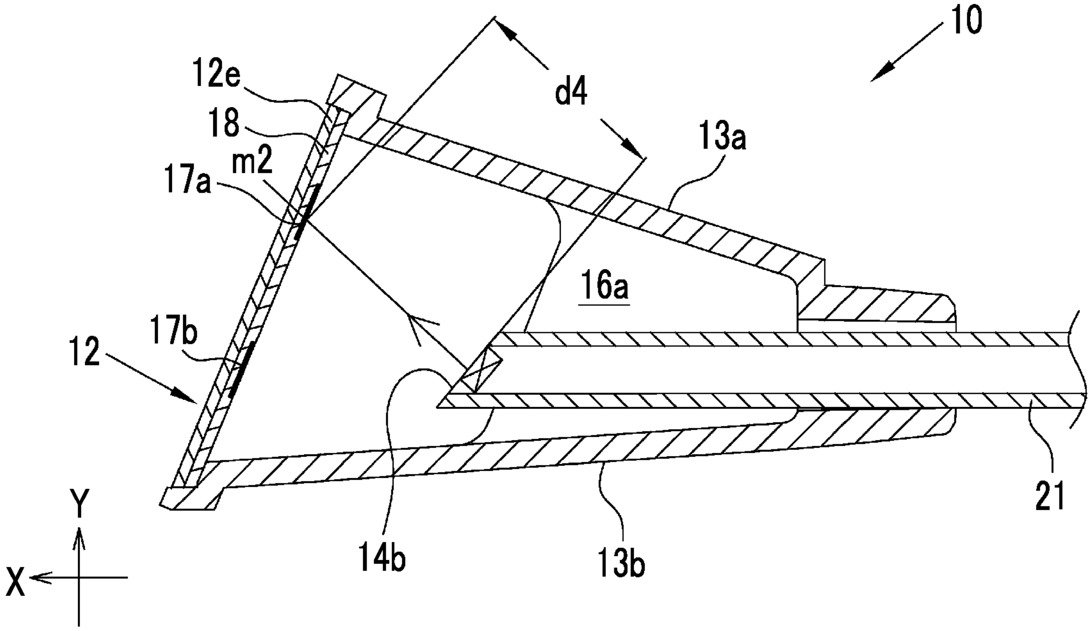
FIG. 20 is a cross-sectional view cut along the line I-I of FIG. 4 and is an explanatory diagram illustrating a distance between a distal end surface in the oblique-viewing endoscope and the chart.

In addition, in order to appropriately perform the white balance adjustment without causing the signal ratio deviation, it is preferable to dispose the distal end part 14*a* so as to have an appropriate distance between the endoscope 14 and the chart 18. The distance between the endoscope 14 and the chart 18 is a distance between the distal end surface 14*b* of the endoscope 14 and the chart 18. As shown in FIG. 19, the distance between the distal end surface 14*b* and the chart 18 in the direct-viewing endoscope 22 is a distance d3. As shown in FIG. 20, the distance between the distal end surface 14*b* and the chart 18 in the oblique-viewing endoscope 21 is a distance d4.

Figure 21:
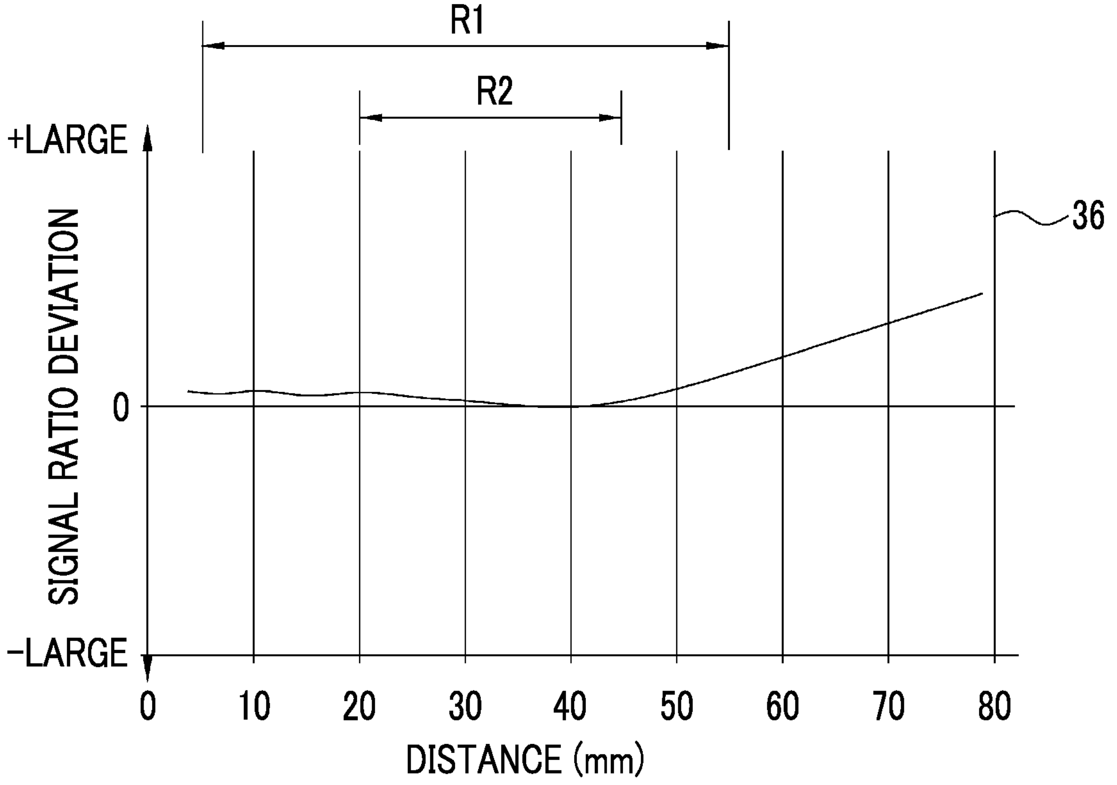
FIG. 21 is a graph showing a relationship between a distance between the distal end surface and the chart, and a signal ratio deviation.

An appropriate distance between the endoscope 14 and the chart 18 can be decided on using measured values using the plurality of types of endoscopes 14 including the direct-viewing endoscope 22 and the oblique-viewing endoscope 21. As shown in FIG. 21, for the plurality of types of endoscopes 14 including the direct-viewing endoscope 22 and the oblique-viewing endoscope 21, white balance adjustment was performed using an endoscope image captured by using the distance d3 or the distance d4 between the distal end surface 14*b* of the endoscope 14 and the surface k of the chart 18 as a distance set in advance. The signal ratio deviation of the endoscope image at that time was represented by a percentage, and a graph 36 was created in which the distance d3 or d4 and the signal ratio deviation were plotted by averaging measured values in the plurality of endoscopes 14, and a range R1 and a range R2 in which the signal ratio deviation does not pose a problem for white balance adjustment were decided on.

From the graph 36, the distance d3 and the distance d4 are preferably in the range R1 and more preferably in the range R2 because the signal ratio deviation is small and there is no problem in the white balance adjustment. Therefore, the distance d3 or the distance d4 between the distal end surface 14*b* of the endoscope 14 and the surface k of the chart 18 is preferably within a range of 5 mm or more and 55 mm or less and more preferably within a range of 20 mm or more and 45 mm or less. In addition, the distance d3 or the distance d4 is preferably 5 mm or more. In a case where an imaging optical system of a general endoscope 14 has a distance d3 or a distance d4 of 5 mm or less, there is a probability that a preferable endoscope image for the white balance adjustment cannot be captured because of the characteristics thereof. From the above, the distance between the distal end surface 14*b* of the endoscope 14 and the surface k of the chart 18 is preferably within a range of 5 mm or more and 55 mm or less. By setting the distance to be within this range, the signal ratio deviation is restrained, and it is possible to acquire an endoscope image with which appropriate white balance adjustment can be performed.

The outer peripheral portion 13 (see FIG. 1) is a portion other than the insertion portion 11 and the lid portion 12 among the portions constituting the adjustment jig 10, and constitutes the adjustment jig 10 by being in contact with each of the insertion portion 11 and the lid portion 12 and forms the internal space 16 of the adjustment jig 10. The outer peripheral portion 13 consists of the upper surface part 13*a*, the bottom surface part 13*b*, the right side surface part 13*c*, and the left side surface part 13*d* (see FIGS. 5 and 6). Since the internal space 16 of the adjustment jig 10 is preferably kept in a dark state in a case where the white balance of the endoscope 14 is adjusted, it is preferable that the outer peripheral portion 13 is connected to the insertion portion 11 and the lid portion 12 such that the external light does not enter the internal space 16. In addition, the adjustment jig 10 may be configured by using a light shielding member. In a case where the adjustment jig 10 is configured by using the light shielding member, the adjustment jig 10 itself may be produced using a material that shields the adjustment jig 10 from light, or a light shielding member may be laminated on a base constituting the adjustment jig 10 by coating, attachment, or the like.

Regarding the light shielding member, the lid portion 12 may include the chart 18 and a light shielding member 41. In a case where the lid portion 12 is disposed to face the insertion portion 11, the chart 18 and the light shielding member 41 are provided in this order from the insertion portion 11 side. As a result, it is possible to more reliably block light entering through the lid portion 12, and appropriate white balance adjustment becomes possible.

In this case, the lid portion 12 itself may be produced using a material that shields the adjustment jig 10 from light. The lid portion 12 includes the lid portion base 12*e* and the chart 18, and the lid portion base 12*e* and/or the chart 18 may be the light shielding member 41 (see FIG. 5). The lid portion base 12*e* functions as a holding portion of the chart 18, and the lid portion 12 is formed by disposing the chart 18 on the lid portion base 12*e*. Further, since the lid portion base 12*e* and/or the chart 18 is the light shielding member 41, the light shielding member 41 other than the lid portion base 12*e* or the chart 18 may not be provided.

Figure 22:
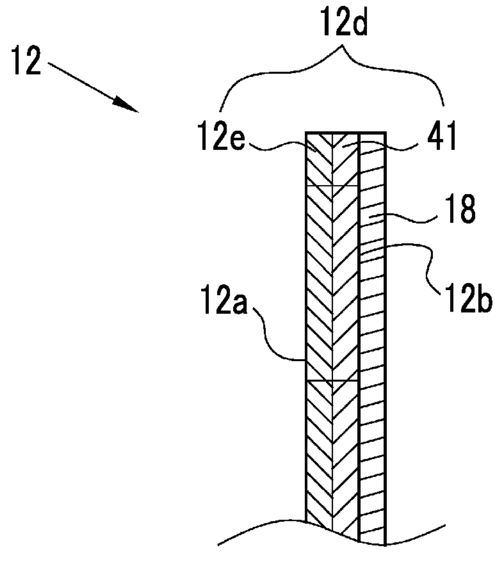
FIG. 22 is an explanatory diagram illustrating a configuration of the lid portion by showing a portion of the lid portion in a cross-sectional view cut along the line I-I of FIG. 4.

As shown in FIG. 22, in a case where the lid portion 12 includes the light shielding member 41, the lid portion 12 may be composed of the lid portion base 12*e*, the light shielding member 41, and the chart 18. In this case, in a connecting member 12*d* in which the lid portion base 12*e* and the light shielding member 41 are laminated, the chart 18 is disposed on a light shielding member 41 side. The connecting member 12*d* of the lid portion base 12*e* and the light shielding member 41 may be formed by bonding plate-like shaped members to each other, or may be formed by applying, attaching, or the like a material forming the light shielding member 41 to the lid portion base 12*e*.

It is preferable that the lid portion 12 is configured such that the chart 18 and the light shielding member 41 are separable from each other. With this, the chart 18 and the light shielding member 41 can be used in combination. In a case where the light shielding member 41 is the connecting member 12*d* laminated with the lid portion base 12*e*, the chart 18 is configured to be separated from the lid portion 12 in which the connecting member 12*d* and the chart 18 are connected to each other. With this, it is possible to select and use, for example, a sterilized and disinfected chart 18 from a plurality of types of charts according to a purpose, and it is possible to quickly perform the white balance adjustment of the plurality of types of endoscopes. As a method of connecting the chart 18 and the light shielding member 41, a method is preferably used in which the chart 18 can be connected to an appropriate position in the light shielding member 41 without causing floating or the like and can be easily separated. For example, in the lid portion 12, the chart 18 and the light shielding member 41 can be configured to be connected to each other by magnetic force, adhesive force, physical attraction force based on the characteristics of the surface to be connected, fitting, or the like. In the present embodiment, a portion of the chart 18, which is connected to the light shielding member 41, is made of a material such as adhesive-capable silicon, and the chart 18 is connected to the light shielding member 41 by physical attraction.

In a case where the chart 18 and the light shielding member 41 are configured to be separated from each other, it is preferable that the position of the chart 18 can be appropriately disposed in the light shielding member 41 for the chart 18 and the light shielding member 41. Therefore, it is preferable that the position of the chart 18 is displayed by a mark or the like on a surface of the light shielding member 41, which is connected to the chart 18.

As shown in FIG. 23, the connecting member 12*d* shown in (a) of FIG. 23 in which the lid portion base 12*e* and the light shielding member 41 are connected to each other, and the chart 18 shown in (b) of FIG. 23 are separable from each other. In order to reconnect the connecting member 12*d* and the chart 18 having a shape different from that of the connecting member 12*d*, a chart position mark 42 may be provided on the surface on the light shielding member 41 side of the connecting member 12*d*, which is a side where the chart 18 is disposed. As a result, in a case where the light shielding member 41 and the chart 18, which have been separated from each other, are connected to each other, the chart 18 can be disposed at an appropriate position by connecting the chart 18 in accordance with the chart position mark 42. In a case where the lid portion base 12*e* and/or the chart 18 is the light shielding member 41, the chart position mark 42 may be provided on a surface of the lid portion base 12*e*, which is a side where the chart 18 is disposed.

Next, an example of the embodiment will be described for the adjustment jig 10, a white balance adjustment method of an endoscope using the adjustment jig 10, and the like. As shown in FIG. 24, the endoscope of the present embodiment is an intra-abdominal endoscope, which is a rigid endoscope (laparoscope) used in endoscopic surgery (laparoscopic surgery), and is a part of an intra-abdominal endoscope system 50 (hereinafter referred to as an endoscope system 50).

The endoscope system 50 comprises an endoscope 51*a* and an endoscope 51*b*, a camera head 52, a light source device 53, a processor device 54, the display 55, and an input device 56. The endoscope system 50 is a system that uses the camera head 52. In the procedure, according to the application or the like, any one of the endoscope 51*a* or the endoscope 51*b* is used by being connected to the light source device 53 and the camera head 52 via a connector 57 for a light source device and a connector 58 for a camera head provided in each of the endoscope 51*a* and the endoscope 51*b*.

The endoscope 51*a* is the direct-viewing endoscope in which the axial direction n and the optical axis direction m of the distal end part 14*a* are parallel to each other (see FIG. 9B), and the endoscope 51*b* is the oblique-viewing endoscope in which the oblique angle $\alpha$ formed by the axial direction n and the optical axis direction m of the distal end part 14*a* is 30 degrees (see FIG. 9A). Further, the outer diameter d2 of the distal end part 14*a* of the endoscope 51*a* is 5 mm (see FIG. 9B), and the outer diameter d1 of the distal end part 14*a* of the endoscope 51*b* is 10 mm (see FIG. 9A). The endoscope 51*a* and the endoscope 51*b* are referred to as an endoscope 51 in a case where these are not distinguished.

The endoscope 51 is a rigid endoscope, is formed to be rigid and elongated, is inserted into a subject under examination, and is used for endoscopic surgery or the like. Before the insertion into the subject under examination, the white balance adjustment is performed for the endoscope 51*a* and the endoscope 51*b*, which are rigid endoscopes. The distal end part 14*a* of the endoscope 51 is inserted into the adjustment jig 10 through the insertion hole 15 during the white balance adjustment, passes through the internal space 16 of the adjustment jig 10, and is advanced to an appropriate position, and images the mark 17 of the chart 18 provided on the inner surface 12*b* of the lid portion 12. Specifically, the endoscope 51*a* is inserted into the second insertion hole 15*b*, and the endoscope 51*b* is inserted by selecting the first insertion hole 15*a*.

An imaging optical system for forming a subject image and an illumination optical system for irradiating the subject with illumination light are provided inside the endoscope 51. The light source device 53 generates illumination light toward the subject during imaging. The illumination light includes excitation light and the like. The light source device 53 includes, for example, a light source unit (not shown) consisting of a light source of a laser diode, a light emitting diode (LED), a xenon lamp, or a halogen lamp and emits at least a white illumination light or an excitation light to be used to emit the white illumination light. In addition, the light source unit includes, as necessary, a phosphor that emits light by being irradiated with excitation light, an optical filter that adjusts a wavelength range, a spectrum, a light intensity, or the like of illumination light or excitation light, or the like. In addition, the light source unit emits light necessary for capturing an image to be used to emphasize a specific tissue or the like, light of which a spectrum is adjusted, or the like in order to calculate biological information such as oxygen saturation of hemoglobin contained in the subject.

The camera head 52 comprises an imaging sensor or the like and images the subject. The processor device 54 comprises a central controller 54*a*, an image processing unit 54*b*, and a display controller 54*c* and performs system control of the endoscope system 50, image processing, and the like. The central controller 54*a* performs system control of the endoscope system 50 in an integrated manner. The image processing unit 54*b* acquires the endoscope image acquired by the imaging sensor of the camera head 52 and generates various images. The image processing unit 54*b* also performs the white balance adjustment and various types of processing related to the white balance adjustment. The display controller 54*c* performs control to display the image generated by the image processing unit 54*b* on the display 55 or the like. The display 55 is a display unit that displays the image captured by the endoscope 51. The input device 56 is a console or the like and is an input device for inputting a setting or the like to the processor device 54 or the like.

Next, an example of a flow of performing white balance adjustment of the endoscope 51 using the adjustment jig 10 of the embodiment of the present invention in the endoscope system 50 will be described using the flowchart shown in FIG. 25. In a case where the endoscope system 50 is used for the procedure, the user performs the white balance adjustment for each of the endoscopes 51 using the adjustment jig 10 before actually using the endoscope 51. The lid portion 12 that includes an appropriate chart 18 corresponding to the endoscope 51 for which the white balance adjustment is performed and the lid portion base 12*e* consisting of the light shielding member 41 is prepared (step ST110). In a case where the white balance adjustment is performed for the plurality of types of endoscopes 51, a chart 18 having all the marks 17 corresponding to the plurality of types of endoscopes 51, respectively, is prepared. The lid portion base 12*e* and the chart 18 are pre-treated with sterilization or the like. The lid portion base 12*e*, which is the light shielding member 41, and the chart 18 are connected to each other to form the lid portion 12. Next, the lid portion 12 is connected to the outer peripheral portion 13 to form the adjustment jig 10 (step ST120).

In a case where the plurality of insertion holes 15 are provided in the adjustment jig 10, an insertion hole 15 corresponding to the outer diameter of the distal end part 14*a* is selected, and the distal end part 14*a* is inserted into the selected insertion hole 15. Here, the white balance adjustment is first performed for the endoscope 51*a*, which is the direct-viewing endoscope 22, and then performed for the endoscope 51*b*, which is the oblique-viewing endoscope 21.

First, an insertion hole 15*b* of the adjustment jig 10 is selected based on the outer diameter of the distal end part 14*a* of the endoscope 51*a*, and the distal end part 14*a* of the endoscope 51*a* is inserted (step ST130). The user may place and hold the adjustment jig 10 on one hand and insert the distal end part 14*a* into the insertion hole 15 of the adjustment jig 10 with the other hand, or may insert the distal end part 14*a* into the insertion hole 15 of the adjustment jig 10 in a state in which the adjustment jig 10 is placed on a desk or the like. The insertion is performed while imaging the mark 17 of the chart 18 provided on the inner surface 12*b* of the lid portion 12. The user gradually inserts the distal end part 14*a* deeper into the adjustment jig 10 while viewing the display 55, thereby advancing the distal end part 14*a* to reach an appropriate distance between the distal end part 14*a* and the chart 18. The endoscope image obtained by imaging the mark 17 is sent to the processor device 54 and is controlled to be displayed on the display 55 by the display controller 54*c*. While observing the endoscope image shown on the display 55, the user inserts the distal end part 14*a* to a position where the position and the size of the mark 17 are appropriately shown in the endoscope image (step ST140).

In the present embodiment, the mark 17 is a circular shape drawn by being filled with a reference color. As shown in FIGS. 26A to 26C, the color, the shape, and the like of the mark 17 shown in the endoscope image displayed on the display 55 are different depending on the position of the distal end part 14*a* in the internal space 16. As shown in FIG. 26A, with the insertion of the distal end part 14*a*, the endoscope image acquired by the endoscope 51 starts to be displayed as a video on the display 55. The mark 17*d* in the endoscope image starts to be displayed in a small and dark color. Next, as the distal end part 14*a* is advanced, as shown in FIG. 26B, the mark 17*d* is shown larger and brighter than in the case of FIG. 26A. The size of the mark 17 shown in the endoscope image in a case where the position of the distal end surface 14*b* is at an appropriate distance from the chart 18 for the white balance adjustment is set in advance, which allows the user to grasp the size of the mark in advance. Then, the distal end part 14*a* is further advanced, and as shown in FIG. 26C, the mark 17*d* is shown with a substantially set size. In this case, in the endoscope image shown on the display 55, the mark 17*d* is displayed in white, which is a bright reference color.

In a case where the mark 17*d* is shown with a substantially set size, the position of the distal end surface 14*b* here is at an appropriate distance from the chart 18 in a case of performing the white balance adjustment. Therefore, in a case where the position of the mark 17 shown in the endoscope image is shown in the substantially central part of the endoscope image and the state as shown in FIG. 26C is obtained, the advancement of the distal end part 14*a* is stopped. The distal end part 14*a* is returned in a case where the distal end part 14*a* is advanced too much, and the distal end part 14*a* is advanced in a case where the distal end part 14*a* is returned too much. By moving the distal end part 14*a* in a back-and-forth motion and repeating these while viewing the display 55, an appropriate distance between the distal end part 14*a* of the endoscope and the chart 18 can be adjusted. In addition, the position of the mark 17 in the horizontal direction can be adjusted by adjusting the direction of the distal end part 14*a* to the left and right such that the mark 17 is shown near the center of the endoscope image. As described above, appropriately showing the mark 17 refers to a state in which the position and the size of the mark 17 shown in the endoscope image are appropriate, and refers to, for example, a case where the center of the mark 17 is aligned with the center of the endoscope image and the entire mark 17 is shown so as to fit exactly within the endoscope image.

At a position where the shape of the mark 17 is appropriately shown, the distal end part 14*a* is kept stationary without further advancing, retracting, or moving in the horizontal direction or the like. In a case where the distal end part 14*a* is at this position, the chart 18 can be appropriately imaged, and appropriate white balance adjustment becomes possible. Therefore, the white balance (WB) adjustment is performed here (step ST150).

The white balance adjustment is performed by the image processing unit 54*b*. In a case where the white balance adjustment is ended, the display controller 54*c* displays on the display 55 that the white balance adjustment is ended, based on a signal from the image processing unit 54*b*. In a case where the white balance adjustment is ended, the user pulls out the distal end part 14*a* from the second insertion hole 15*b* (step ST160). In a case where the white balance adjustment of another endoscope is subsequently performed (Y in step ST170), the endoscope 51*a* is removed from the camera head 52 and the light source device 53 and is replaced with the endoscope 51*b*, instead (step ST180).

Next, in order to perform the white balance adjustment for the endoscope 51*b*, which is the oblique-viewing endoscope 21, an insertion hole 15*a* of the adjustment jig 10 is selected based on the outer diameter of the distal end part 14*a* of the endoscope 51*b*, the distal end part 14*a* of the endoscope 51*b* is inserted (step ST130), and the white balance adjustment is carried out in the same manner as in the case of the endoscope 51*a*. In a case where there are the plurality of endoscopes 51, the white balance adjustment is completed by performing the white balance adjustment for all the endoscopes 51 that require the white balance adjustment. In a case where the white balance adjustment of another endoscope is not subsequently performed (N in step ST170), the white balance adjustment is completed.

In the adjustment jig 10 configured as described above, since the chart 18 is inclined with respect to the perpendicular plane j perpendicular to the insertion direction X of the distal end part 14*a*, and the chart 18 is provided with the plurality of marks 17, the chart 18 can be imaged under appropriate imaging conditions regardless of whether the endoscope is the direct-viewing endoscope or the oblique-viewing endoscope.

As described above, with the adjustment jig 10, an appropriate insertion hole and an appropriate mark 17 for each of the endoscopes can be used regardless of a difference between the direct-viewing endoscope 22 and the oblique-viewing endoscope 21 and a difference between the outer diameter d1 and the outer diameter d2 of the distal end parts 14*a*, and the mark 17 can be imaged by easily disposing the imaging lens of the endoscope at an appropriate position. Therefore, the adjustment jig 10 can easily perform appropriate white balance adjustment for any of the plurality of types of endoscopes distinguished by the difference between the direct-viewing endoscope 22 and the oblique-viewing endoscope 21, and the difference between the outer diameter d1 and the outer diameter d2 of the distal end parts 14*a*.

In addition, in a case where two or more insertion holes 15 having inner diameters different from each other are provided, an insertion hole 15 having an appropriate inner diameter is selected, and the distal end part 14*a* is inserted thereinto even in the plurality of types of endoscopes having outer diameters different from each other, so that the chart 18 can be imaged after the distance between the distal end surface 14*b* of the endoscope and the chart 18 and the position of the distal end surface 14*b* are precisely adjusted. In this case, since the chart 18 is provided with the mark 17 at a position corresponding to each of the insertion holes 15, the corresponding mark 17 is imaged even in a case where any of the insertion holes 15 is used, whereby the mark 17 for appropriately performing the white balance adjustment can be imaged. Therefore, for example, in a case where the white balance adjustment is performed immediately before the procedure for each case in which a set of a plurality of types of direct-viewing endoscopes 22 and oblique-viewing endoscopes 21 having outer diameters different from each other is used, the position of the distal end part 14*a* is appropriately adjusted through an easy method, such as using the adjustment jig 10, to which the chart 18 having the plurality of marks 17 appropriate for all the respective endoscopes included in this set is attached, and inserting the distal end part 14*a* to reach a distance in which the shape of the mark 17 shown in the display is appropriately shown, and then white balance adjustment can be sequentially and accurately completed for the plurality of endoscopes 14.

Since the chart 18 is provided with the mark 17, it is possible to optimize the distance between the distal end surface 14*b* and the chart 18 during the white balance adjustment. Since the mark 17 is imaged for the white balance adjustment, the mark 17 has a reference color necessary for the white balance adjustment. Therefore, it is also conceivable to configure the entire chart 18 with a reference color. However, by configuring the chart 18 to have the mark 17 consisting of a specific shape, the distance between the distal end surface 14*b* and the chart 18 can be more precisely adjusted using the shape of the mark 17 in the endoscope image, such as the size and the form, and precise white balance adjustment can be performed.

In a case where the lid portion 12 and the outer peripheral portion 13 are separably connected to each other, by preparing a plurality of charts 18 according to the types of endoscopes, the accuracy of the white balance adjustment, the purpose of white balance adjustment, and the like, it is possible to immediately prepare the adjustment jigs 10 corresponding to various situations only by connecting the lid portion 12 having a desired chart 18. Therefore, the distal end part 14*a* to be inserted into the insertion hole 15 may be the distal end part 14*a* of the rigid endoscope. In addition, it is also possible to use the chart 18 prepared for each set of the rigid endoscopes to be used for a specific procedure, and it is possible to quickly perform appropriate white balance adjustment for each of the plurality of rigid endoscopes to be used, before the specific procedure.

In addition, in a case where the lid portion 12 and the outer peripheral portion 13 are separably connected to each other, the chart 18 provided in the lid portion 12 can be easily changed by separating the lid portion 12. In addition, disinfection, sterilization, and the like of the lid portion 12 and the inside of the adjustment jig 10 can be appropriately performed.

As described above, the adjustment jig 10 is a white balance adjustment jig for an endoscope capable of facilitating appropriate white balance adjustment for any of a plurality of types of endoscopes.

Second Embodiment

In the adjustment jig 10 of the first embodiment, the lid portion 12 and the outer peripheral portion 13 are connected to each other by magnetic force, but in an adjustment jig 60 of a second embodiment, a lid portion 62 and an outer peripheral portion 63 are connected to each other by fitting. Since the adjustment jig 60 of the second embodiment is the same as that of the first embodiment except that the lid portion 62 and the outer peripheral portion 63 are connected to each other by fitting, the description of the same portion will be omitted. The lid portion 62 and the outer peripheral portion 63 each have a configuration for fitting each other. In the present embodiment, a slit type is used for fitting the lid portion 62 and the outer peripheral portion 63. The lid portion 62 is connected to a portion of the outer peripheral portion 63, which comes into contact with the lid portion 62, through sliding using a slit.

As shown in FIG. 27, at a position where the lid portion 62 comes into contact, the outer peripheral portion 63 includes slit projections 71 at an upper end part and a lower end part that are both end parts in the vertical direction Y. Further, guide protruding portions 72 are provided on a left end part and a right end part that are both end parts in the width direction Z. In addition, stoppers 73 that prevent the sliding of the lid portion 62 are provided at the upper end part and the lower end part in correspondence with stop members 74 (see FIG. 28C) provided in the lid portion 62.

As shown in FIGS. 28A to 28C, the lid portion 62 has slits 76 formed by slit forming portions 75. The slit projection 71 of the outer peripheral portion 63 is fitted into the slit 76 while sliding. In addition, a guide recessed portion 77 is provided on a side of the lid portion 62 facing the internal space 16 (see FIG. 28B or FIG. 28C). The guide recessed portion 77 is configured to have a shape corresponding to the guide protruding portion 72 of the outer peripheral portion 63. In addition, the lid portion 62 includes a direction display 78 indicating a direction of the slide. The lid portion 62 and the outer peripheral portion 63 can be easily connected to each other by sliding the slit projection 71 into the slit 76 in the direction indicated by the direction display 78 while viewing an outer surface 62*a* of the lid portion 62.

As shown in FIGS. 28B and 28C, the lid portion 62 includes the chart 18 on an inner surface 62*b* facing the internal space 16. As shown in FIG. 28C, the chart 18 has the marks 17*a*, 17*b*, 17*c*, and 17*d* which are each formed in a circular shape with a reference color. It is preferable that the chart 18 is separable from the lid portion 62 and the like as in the first embodiment.

As shown in (a) of FIG. 29, in a case where the lid portion 62 and the outer peripheral portion 63, which are separated from each other, are connected to each other, the slit projection 71 of the outer peripheral portion 63 is fitted into the slit 76 of the lid portion 62, the lid portion 62 and the outer peripheral portion 63 are aligned with each other such that the guide recessed portion 77 of the lid portion 62 and the guide protruding portion 72 of the outer peripheral portion 63 are aligned with each other, and the lid portion 62 is slid in the direction indicated by the direction display 78 of the lid portion 62. Specifically, the lid portion 62 and the outer peripheral portion 63 are fitted with each other by sliding the lid portion 62 toward the outer peripheral portion 63 from the left side when viewed from the outer surface 62*a* of the lid portion 62. As shown in (b) of FIG. 29, in a case where the lid portion 62 is slid, the lid portion 62 can be disposed at an appropriate position by sliding the lid portion 62 until the stop members 74 provided in the lid portion 62 is limited by the stoppers 73 provided in the outer peripheral portion 63.

As described above, by connecting the lid portion 62 and the outer peripheral portion 63 to each other by fitting, it is possible to connect the lid portion 62 and the outer peripheral portion 63 such that a gap therebetween can be minimized. In addition, providing the stoppers 73 and the stop members 74 makes it easy to appropriately dispose and connect the positions of the lid portion 62 in the width direction Z, which is the insertion direction, and providing the guide protruding portions 72 and the guide recessed portion 77 makes it easy to appropriately dispose and connect the positions of the lid portion 62 in the vertical direction Y when inserting the lid portion 62. As described above, it is easy to dispose the separated lid portion 62 at a correct position of the outer peripheral portion 63 to form the adjustment jig 60.

Third Embodiment

In the first embodiment and the second embodiment, the lid portion 12 and the lid portion 62 each have a plate-like shape, but in an adjustment jig 80 of a third embodiment, a lid portion 82 has a triangular prism shape rather than a plate-like shape. Since the adjustment jig 80 of the third embodiment is the same as that of the first embodiment except that the lid portion 82 is not in a plate-like shape, the description thereof will be omitted.

The lid portion 82 of the adjustment jig 80 has a triangular prism shape for fixing the adjustment jig 80 to a wall, a wagon, a shelf, a floor, or the like. In the adjustment jig 10 in the first embodiment and the adjustment jig 60 in the second embodiment, the distal end part 14*a* is inserted into the insertion hole 15 by, for example, holding the adjustment jig 10 or 60 in the left hand and holding the endoscope 14 in the right hand, but in the adjustment jig 80, it is not necessary to always hold the adjustment jig 80 by hand. Therefore, for example, another operation can be performed, such as holding the endoscope 14 in the right hand and operating the input device 56 with the left hand. The adjustment jig 80 or the like may be fixed using a portion other than the lid portion 62, and for example, the bottom surface part 13*b* or the like may be fixed.

As shown in FIG. 30, the adjustment jig 80 may be fixed to a wall 81 of the desk because the lid portion 82 has a triangular prism shape. As a result, it is possible to hold the endoscope 14 while placing one hand on a desk 83 and to insert the distal end part 14*a* into the insertion hole 15. In addition, as shown in FIG. 31, the lid portion 82 may be fixed to a desk, a shelf, or a floor. In this case, it is preferable that the insertion hole 15 is open in a direction other than the vertical direction such that the entry of light into the internal space 16 of the adjustment jig 80 through the insertion hole 15 is minimized.

Fourth Embodiment

In the first embodiment, the adjustment or determination is performed by allowing the user to grasp in advance the position and the size of the mark 17 shown on the display 55, but in the fourth embodiment, the position and the size of the mark 17 shown on the display 55 are determined using a determination display 91 displayed on the display 55. Since the display 55 of the fourth embodiment is the same as that of the first embodiment except that the determination display 91 is displayed, the description thereof will be omitted.

It is preferable that the determination display 91 displayed on the display 55 corresponds to the shape of the mark 17. In a case where the mark 17 is circular, the determination display 91 is also circular. The user can easily grasp how to adjust the position of the distal end part 14*a* by adjusting the position of the distal end part 14*a* inside the adjustment jig 10 such that the mark 17 appropriately falls within the determination display 91 during the white balance adjustment, which makes it easy to appropriately dispose the distal end part 14*a* in the internal space 16 and to perform appropriate white balance adjustment.

As shown in FIGS. 32A to 32D, in the present embodiment, since the mark 17 is circular, the determination display 91 has a donut-like shape in which the inside of a double circle is displayed in color. In the endoscope image, by adjusting the position and the size of the mark 17 using the determination display 91 as a reference, the position of the distal end part 14*a* inside the adjustment jig 10 can be appropriately disposed. As shown in FIG. 32A, it is assumed that, in a case where the position of the distal end part 14*a* is adjusted such that the mark 17 completely concentrically falls within the determination display 91 shown on the display 55 when the distal end part 14*a* is inserted into the adjustment jig 10, the position of the distal end part 14*a* inside the adjustment jig 10 is appropriate.

As shown in FIG. 32B, in a case where the mark 17 is shown smaller than the determination display 91 and does not appropriately overlap, it is known that the user need only adjust the mark 17 to be shown larger by further inserting the distal end part 14*a*. As shown in FIG. 32C, in a case where the mark 17 is shown larger than the determination display 91 and does not appropriately overlap, it is known that the user need only adjust the mark 17 to be shown smaller by retracting the distal end part 14*a*. As shown in FIG. 32D, in a case where the mark 17 deviates from the determination display 91 and does not appropriately overlap, it is known that the user need only adjust the mark 17 to correctly overlap with the determination display 91 by adjusting the direction of the distal end part 14*a*. More specifically, in this case, since the size of the mark 17 is appropriate and the distance between the distal end part 14*a* and the chart 18 is appropriate, and the distance between the distal end part 14*a* and the chart 18 is appropriate, it is known that the user need only adjust only the direction of the distal end part 14*a* without moving the position of the distal end part 14*a* in the insertion direction X.

In the present embodiment, in a case where there is a problem in the position and the size of the mark 17 with the determination display 91 as a reference in the endoscope system 50, the user determines that there is a problem in the position and the size of the mark 17, but determination may be made by means other than the user. That is, the endoscope system 50 may be configured to issue a notification in a case where there is a problem in the position and the size of the mark 17 with the determination display 91 as a reference. The notification need only be in a form that can be recognized by the user and can be, for example, a sound, a display on the display 55, or the like. In addition, the notification may be issued in a case where there is no problem in the position and the size of the mark 17. For example, a first notification may be issued in a case where the positional relationship of the mark 17 becomes appropriate, and a second notification may be issued upon completion of the white balance adjustment, after waiting for the user to fix the distal end part 14*a* as it is and complete the white balance adjustment. It is preferable that the first notification and the second notification allow the user to recognize the difference, such as changing the tone or changing the manner of sound.

In a case of issuing a notification, the determination display 91 may or may not be displayed. That is, the position of the distal end part 14*a* may be determined by the image processing unit 54*b* based on the position and the size of the mark 17 shown in the endoscope image. A notification indicating that an instruction as to how to move the distal end part 14*a* may be issued based on the determination of the image processing unit 54*b*. The determination by the image processing unit 54*b* can be performed by a known image processing technique, and the determination may be made by a learning model in a machine learning technique, which has learned the position and the size of the mark 17 shown in the endoscope image.

In addition, in the endoscope system 50, a configuration may be employed in which, in a case where the position of the distal end part 14*a* inserted into the adjustment jig 10 becomes appropriate when the white balance adjustment using the adjustment jig 10 is performed for the endoscope, the endoscope image is automatically recorded in a recording unit (not shown) or the like provided in the processor device 54. With this, the user does not need to hold the position of the distal end part 14*a* and wait for the completion of the white balance adjustment, in a case where the position of the distal end part 14*a* becomes appropriate. That is, the image processing unit 54*b* can use the recorded endoscope image to appropriately perform the white balance adjustment, for example, after acquiring the endoscope image. In particular, in a case where an individual identification number of the used endoscope 14 is recorded in the endoscope image, the white balance adjustment is performed later by sequentially recording appropriate endoscope images using each of the plurality of types of endoscopes 14 and the adjustment jig 10, so that appropriate white balance adjustment is automatically performed for each of the plurality of types of endoscopes. Therefore, even in a case where the white balance adjustment is performed in a large number of endoscopes 14 of a plurality of types, the white balance adjustment can be quickly and appropriately performed.

In the above-described embodiments, the hardware structures of processing units that execute various types of processing, such as the central controller 54*a*, the image processing unit 54*b*, and the display controller 54*c*, are various processors to be described below. The various processors include a central processing unit (CPU) that is a general-purpose processor which executes software (programs) to function as various processing units, a graphical processing unit (GPU), a programmable logic device (PLD) that is a processor having a changeable circuit configuration after manufacture, such as a field programmable gate array (FPGA), a dedicated electrical circuit that is a processor having a dedicated circuit configuration designed to execute various types of processing, and the like.

One processing unit may be composed of one of the various processors or may be composed of a combination of two or more processors of the same type or different types (for example, a combination of a plurality of FPGAs, a combination of a CPU and an FPGA, or a combination of a CPU and a GPU). Alternatively, a plurality of processing units may be composed of one processor. A first example in which a plurality of processing units are composed of one processor is an aspect in which one or more CPUs and software are combined to constitute one processor and the processor functions as a plurality of processing units, as represented by a computer, such as a client or a server. A second example of the configuration is an aspect in which a processor that realizes all the functions of a system including a plurality of processing units with one integrated circuit (IC) chip is used, as represented by a system on chip (SoC). As described above, various processing units are composed of one or more of the above-described various processors, as the hardware structure.

Furthermore, as the hardware structures of the various processors, more specifically, electrical circuitry obtained by combining circuit elements, such as semiconductor elements, may be used. Further, the hardware structure of the storage unit is a storage device, such as a hard disc drive (HDD) or a solid state drive (SSD).

From the above description, it is possible to grasp the endoscope system described in Appendix 1 or Appendix 2.

Appendix 1

An endoscope system comprising:
- an endoscope that images a subject;
- a processor device that acquires an endoscope image captured by the endoscope; and
- a display that displays the endoscope image,
- in which the processor device performs, in a case where the endoscope image in which a mark of a chart provided in a white balance adjustment jig for an endoscope is imaged as the subject is displayed on the display, control to superimpose and display, on the endoscope image, a determination display for determining a position and a size of the mark in the endoscope image,
- the white balance adjustment jig for an endoscope includes
  - an insertion portion that is provided with at least one insertion hole into which a distal end part of the endoscope is inserted,
  - a lid portion that is disposed to face the insertion portion in an insertion direction of the distal end part, and
  - an outer peripheral portion that is in contact with the insertion portion and the lid portion to form an internal space with the insertion portion and the lid portion,
- the lid portion includes the chart having a plurality of the marks on an inner surface facing the internal space, and
- the chart is inclined with respect to a perpendicular plane perpendicular to the insertion direction.

Appendix 2

An endoscope system comprising:
- an endoscope that images a subject;

a processor device that acquires an endoscope image captured by the endoscope; and a display that displays the endoscope image, in which the processor device determines whether or not the endoscope image is appropriate for white balance adjustment based on the endoscope image in which a mark of a chart provided in a white balance adjustment jig for an endoscope is imaged as the subject, the white balance adjustment jig for an endoscope includes an insertion portion that is provided with at least one insertion hole into which a distal end part of the endoscope is inserted, a lid portion that is disposed to face the insertion portion in an insertion direction of the distal end part, and an outer peripheral portion that is in contact with the insertion portion and the lid portion to form an internal space with the insertion portion and the lid portion, the lid portion includes the chart having a plurality of the marks on an inner surface facing the internal space, and the chart is inclined with respect to a perpendicular plane perpendicular to the insertion direction.

EXPLANATION OF REFERENCES

10, 60, 80: adjustment jig
11: insertion portion
11*a*, 11*b*: guide part
12, 62, 82: lid portion
12*a*, 62*a*: outer surface
12*b*, 62*b*: inner surface
12*c*: protruding portion
12*d*: connecting member
12*e*: lid portion base
13, 63: outer peripheral portion
13*a*: upper surface part
13*b*: bottom surface part
13*c*: right side surface part
13*d*: left side surface part
13*e*: partition
13*f*: magnet insertion portion
13*g*: recessed portion
14*a*: distal end part
14*b*: distal end surface
14*c*: large diameter endoscope
14*d*: small diameter endoscope
15*a*: first insertion hole
15*b*: second insertion hole
16*a*, 16*b*: internal space
17*a*, 17*b*, 17*c*, 17*d*: mark
18: chart
21: oblique-viewing endoscope
22: direct-viewing endoscope
31, 32, 33, 34: region
35, 36: graph
41: light shielding member
42: chart position mark
50: endoscope system
51*a*, 51*b*: endoscope
52: camera head
53: light source device
54: processor device
54*a*: central controller
54*b*: image processing unit
54*c*: display controller
55: display
56: input device
57: connector for light source device
58: connector for camera head
71: slit projection
72: guide protruding portion
73: stopper
74: stop member
75: slit forming portion
76: slit
77: guide recessed portion
78: direction display
81: wall
83: desk
91: determination display
d1, d2: outer diameter
α: oblique angle
β, β1, β2: inclination angle
d3, d4: distance
m, m1, m2: optical axis direction
n: axial direction of distal end part
k: surface of chart
l: perpendicular plane perpendicular to optical axis direction
j: perpendicular plane perpendicular to insertion direction
R1, R2: range
Y: vertical direction
Z: width direction
ST110 to ST180: step

What is claimed is:

1. A white balance adjustment jig for an endoscope, comprising:

an insertion portion that includes at least one insertion hole into which a distal end part of an endoscope is inserted;

a lid portion that is disposed to face the insertion portion in an insertion direction of the distal end part; and an outer peripheral portion that is in contact with the insertion portion and the lid portion to form an internal space with the insertion portion and the lid portion, wherein the outer peripheral portion is in contact with the lid portion by fitting a protruding portion formed on the lid portion into a recessed portion formed on the outer peripheral portion, wherein the lid portion includes a chart having a plurality of marks on an inner surface facing the internal space, the chart is inclined with respect to a perpendicular plane perpendicular to the insertion direction, wherein the insertion portion includes a plurality of the insertion holes, and the internal space is partitioned according to each of the insertion holes, and wherein the outer peripheral portion includes a partition wall extending from a position of the insertion portion to a position of the inner surface of the lid portion to partition the internal space into a plurality of internal spaces corresponding to each of the insertion holes.

2. The white balance adjustment jig for an endoscope according to claim 1, wherein the chart is inclined at an angle within a range of 5 degrees or more and 40 degrees or less with respect to the perpendicular plane.

3. The white balance adjustment jig for an endoscope according to claim 1, wherein the chart is inclined at an angle within a range of 15 degrees or more and 30 degrees or less with respect to the perpendicular plane.

4. The white balance adjustment jig for an endoscope according to claim 1, wherein the chart is inclined toward an insertion portion side.

5. The white balance adjustment jig for an endoscope according to claim 2, wherein the angle is an angle in a case where an inclination toward an insertion portion side is defined as positive with a lower part of the chart in use as an axis.

6. The white balance adjustment jig for an endoscope according to claim 1, wherein the chart is inclined at an angle within a range of 5 degrees or more and 40 degrees or less with respect to a perpendicular plane perpendicular to an optical axis of the endoscope in a case where an inclination toward an insertion portion side is defined as positive with a lower part of the chart in use as an axis.

7. The white balance adjustment jig for an endoscope according to claim 1, wherein the chart is inclined at an angle within a range of 15 degrees or more and 30 degrees or less with respect to the perpendicular plane in a case where an inclination toward an insertion portion side is defined as positive with a lower part of the chart in use as an axis.

8. The white balance adjustment jig for an endoscope according to claim 1, wherein the plurality of marks are disposed in the chart along the insertion direction.

9. The white balance adjustment jig for an endoscope according to claim 1, wherein one of the plurality of marks is disposed at a position where the chart and an optical axis direction of the endoscope to be inserted into the insertion hole intersect with each other.

10. The white balance adjustment jig for an endoscope according to claim 1, wherein the plurality of insertion holes have inner diameters different from each other.

11. The white balance adjustment jig for an endoscope according to claim 1, wherein the lid portion and the outer peripheral portion are separably connected to each other.

12. The white balance adjustment jig for an endoscope according to claim 1, wherein the lid portion and the outer peripheral portion are separably connected to each other by magnetic force and/or fitting.

13. The white balance adjustment jig for an endoscope according to claim 1, wherein the lid portion includes the chart and a light shielding member, and in a case where the lid portion is disposed to face the insertion portion, the chart and the light shielding member are provided in this order from an insertion portion side.

14. The white balance adjustment jig for an endoscope according to claim 13, wherein the lid portion is configured such that the chart and the light shielding member are separable from each other.

15. The white balance adjustment jig for an endoscope according to claim 14, wherein the lid portion includes a lid portion base and the chart, and the light shielding member is the lid portion base.

16. The white balance adjustment jig for an endoscope according to claim 1, wherein the endoscope is a rigid endoscope.

17. The white balance adjustment jig for an endoscope according to claim 1, wherein the endoscope is a direct-viewing endoscope or an oblique-viewing endoscope.

18. The white balance adjustment jig for an endoscope according to claim 1, wherein the mark has a reference color.

19. A white balance adjustment method for an endoscope using a white balance adjustment jig for an endoscope, the white balance adjustment jig including:

an insertion portion that includes at least one insertion hole into which a distal end part of an endoscope is inserted;

a lid portion that is disposed to face the insertion portion in an insertion direction of the distal end part; and an outer peripheral portion that is in contact with the insertion portion and the lid portion to form an internal space with the insertion portion and the lid portion, wherein the outer peripheral portion is in contact with the lid portion by fitting a protruding portion formed on the lid portion into a recessed portion formed on the outer peripheral portion, the lid portion including a chart having a plurality of marks on an inner surface facing the internal space, and the chart being inclined with respect to a perpendicular plane perpendicular to the insertion direction, wherein the insertion portion includes a plurality of the insertion holes, and the internal space is partitioned according to each of the insertion holes, and wherein the outer peripheral portion includes a partition wall extending from a position of the insertion portion to a position of the inner surface of the lid portion to partition the internal space into a plurality of internal spaces corresponding to each of the insertion holes, the white balance adjustment method comprising:

inserting the distal end part of the endoscope including an imaging unit that images a subject into the insertion hole;

imaging the mark using the imaging unit; and adjusting white balance of the endoscope using an image showing the mark, which is obtained through imaging.

20. The white balance adjustment method for an endoscope according to claim 19, wherein the endoscope is a direct-viewing endoscope or an oblique-viewing endoscope.

21. The white balance adjustment method for an endoscope according to claim 19, wherein the white balance adjustment jig for an endoscope includes a plurality of the insertion holes, and the distal end part is inserted into the insertion hole selected from the plurality of insertion holes according to an outer diameter of the distal end part.

22. The white balance adjustment method for an endoscope according to claim 19, wherein the mark is imaged after adjusting a position and a shape of the mark shown in the image.

* * * * *